US008618295B2

(12) United States Patent
Shiu et al.

(10) Patent No.: US 8,618,295 B2
(45) Date of Patent: Dec. 31, 2013

(54) PREPARATION OF LUMINESCENT IRIDIUM COMPLEXES AND PRECURSORS THEREOF

(75) Inventors: Kom-Bei Shiu, Taichung (TW); Wu-Sian Sie, Tainan (TW)

(73) Assignee: National Chen Kung University (TW)

( * ) Notice: Subject to any disclaimer, the term of this patent is extended or adjusted under 35 U.S.C. 154(b) by 299 days.

(21) Appl. No.: 13/064,401

(22) Filed: Mar. 23, 2011

(65) Prior Publication Data
US 2011/0251391 A1 Oct. 13, 2011

(30) Foreign Application Priority Data

Apr. 12, 2010 (TW) .............................. 99111329 A

(51) Int. Cl.
*C07F 15/00* (2006.01)
*C07D 217/02* (2006.01)
(52) U.S. Cl.
USPC .............................................. 546/2; 546/139
(58) Field of Classification Search
USPC ..................................................... 546/2, 139
See application file for complete search history.

(56) References Cited

U.S. PATENT DOCUMENTS 7,923,521 B2 * 4/2011 Stoessel et al. ................... 528/9

FOREIGN PATENT DOCUMENTS

JP 2004168758 * 6/2004 ............. C07F 15/00

OTHER PUBLICATIONS

Vladimir V. Grushin, Norman Herron, Daniel D. Lecloux, William J. Marshall, Viacheslav A. Petrov, and Ying Wang; New, Efficient Electroluminescent Materials Based on Organometallic Ir Complexes; *The Royal Society of Chemistry* 2001; Jul. 23, 2001; p. 1494-p. 1495.
Jacek C. Ostrowski, Matthew R. Robinson, Alan J. Heeger, and Guillermo C. Bazan; Amorphous Iridium Complexes for Electrophosphorescent Light Emitting Devices; *The Royal Society of Chemistry* 2002; Mar. 14, 2002; p. 784-p. 785.
Cheng-Hsien Yang, Kai-Hung Fang, Chun-Hung Chen, and I-Wen Sun; High Efficiency Mer-Iridium Complexes for Organic Light-Emitting Diodes; *The Royal Society of Chemistry* 2004; Aug. 23, 2004; p. 2232-p. 2233.
Hideo Konno and Yoshiyuki Sasaki; Selective One-Pot Synthesis of Facial Tris-Ortho-Metalated Iridium (III) Complexes Using Microwave Irradiation; *The Chemical Society of Japan*; Dec. 12, 2002; p. 252-p. 253; vol. 32 No. 3.

Y Zhang, C. D. Baer, C. Camaioni-Neto, P. O'Brien, and D. A. Sweigart; A New Synthetic Route to the Preparation of a Series of Strong Photoreducing Agents; fac Tris-Ortho-Metalated Complexes of Iridium (III) with Substituted 2-Phenylpyridines; *American Chemical Society*; Dec. 4, 1990; p. 1685-p. 1687.
Mirco G. Colombo, Thomas C. Brunold, Toni Riedener, and Hans U. Gudel; Facial Tris CyclometalatedRh$^{3+}$ and Ir$^{3+}$ Complexes: Their Synthesis, Structure, and Optical Spectroscopic Properties; *American Chemical Society*; Apr. 15, 1993; p. 545-p. 550.
Shouquan Huo, Joseph C. Deaton, Manju Rajeswaran, and William C. Lenhart; Highly Efficient, Selective, and General Method for the Preparation of Meridional Homo- and Heteroleptic Tris-cyclometalated Iridium; American Chemical Society; Jan. 17, 2006; p. 3155-p. 3157; vol. 45, No. 8.
Kari A. McGee and Kent R. Mann; Selective Low-Temperature Syntheses of Facial and Meridional Tris-cyclometalated Iridium (III) Complexes; *American Chemical Society*; Mar. 7, 2007; p. 7800-p. 7809; vol. 46, No. 19.
K. A. King, P. J. Spellane, and R. J. Watts; Excited-State Properties of a Triply Ortho-Metalated Iridium (III) Complex; *American Chemical Society*; Oct. 22, 1984; p. 1431-p. 1432; No. 107.
Arnold B. Tamayo, Bert D. Alleyne, Peter I. Djurovich, Sergey Lamansky, Irina Tsyba, Nam N. Ho, Robert Bau, and Mark E. Thompson; Synthesis and Characterization of Facial and Meridional Tris-cyclometalated Iridium (III) Complexes; *American Chemical Society*; Feb. 6, 2003; p. 7377-p. 7387; No. 125.
Akira Tsuboyama, Hironobu Iwawaki, Manabu Furugori, Taihei Mukaide, Jun Kamatani, Satoshi Igawa, Takashi Moriyama, Seishi Miura, Takao Takiguchi, Shinjiro Okada, Mikio Hoshino, and Kazunori Ueno; Homoleptic Cyclometalated Iridium Complexes with Highly Efficient Red Phosphorescence and Application to Organic Light-Emitting Diode; *American Chemical Society*; Feb. 18, 2003; p. 12971-p.12979; No. 125.
Boerta Ragni, Edward A. Plummer, Klemens Brunner, Johannes W. Hofstraat; Francesco Babudri, Gianluca M. Farinola, Francesco Naso, and Luisa De Cola; Blue Emitting Iridium Complexes: Synthesis, Photophysics and Phosphorescent Devices; *The Royal Society of Chemistry*; Jan. 6, 2006; p. 1161-p. 1170; No. 16.

* cited by examiner

*Primary Examiner* — Charanjit Aulakh
(74) *Attorney, Agent, or Firm* — Bacon & Thomas, PLLC

(57) ABSTRACT

Synthetic processes for preparing luminescent iridium complexes and precursors thereof are provided. The method employs water as the reaction solvent to prepare luminescent iridium complexes in two different ways. In the first way, a precursor [Ir$_2$(C$_{11}$NR$_8$)$_4$I$_2$] (Formula I) is prepared from one of IrCl$_3$, M$_3$IrCl$_6$ (M=Li, Na, K) and [Ir$_2$(C$_{11}$NR$_8$)$_4$Cl$_2$], and then the precursor [Ir$_2$(C$_{11}$NR$_8$)$_4$I$_2$] is converted into one of the two luminescent iridium isomeric complexes [Ir(C$_{11}$NR$_8$)$_2$ (C$_{11}$NR'$_8$)] (Formula II). In the second way, a metal complex IrCl$_3$ or M$_3$IrCl$_6$ (M=Li, Na, K), HC$_{11}$NR$_8$ and a base are converted selectively into one of the two iridium isomeric complexes [Ir(C$_{11}$NR$_8$)$_3$] (Formula VIII). Herein, R and R' are defined the same as the specification.

9 Claims, No Drawings

PREPARATION OF LUMINESCENT IRIDIUM COMPLEXES AND PRECURSORS THEREOF

CROSS REFERENCE TO RELATED APPLICATION

This application claims the benefits of the Taiwan Patent Application Serial Number 099111329, filed on Apr. 12, 2010, the subject matter of which is incorporated herein by reference.

BACKGROUND OF THE INVENTION

1. Field of the Invention

The present invention relates to novel synthetic processes for preparing complexes and, more particularly, to novel synthetic processes for preparing luminescent iridium complexes and precursors thereof.

2. Description of Related Art

In addition to inorganic light emitting diodes (LEDs), organic light emitting diodes (OLEDs) made of organic materials have attracted a great deal of attention for lightening and display applications, and have been applied in many products, such as mobile phones, liquid crystal displays, flexible displays etc., owing to their low cost, reduced weight, compact volume, low operating voltage and flexibility.

Like conventional inorganic light emitting diodes (LEDs), electrons and holes, formed in OLEDs under electric fields generated by applying voltage, will move towards the cathode and the anode, respectively, and then recombine in an organic layer to form excitons capable of radiatively relaxing from their excited state to the ground state.

The wavelength of light emitted from OLEDs depends on energy gap between HOMO and LUMO of emissive organic materials applied in OLEDs. Compounds capable of emitting phosphorescent light include transition metal complexes, such as osmium complexes, iridium complexes, platinum complexes, ruthenium complexes, rhodium complexes etc., which exhibit enhanced luminescence efficiency and have reduced half-life period of phosphorescence.

Among these transition metal complexes, iridium complexes can show high phosphorescence emission at room temperature, and the tris-cyclometalated iridium complex, fac-[Ir(ppy)$_3$], is one of the best green phosphorescent materials and can be used as a phosphorescent dopant in an emissive layer of an OLED. Tamayo et al. (Tamayo et al., 2003) published synthesis of fac-[Ir(ppy)$_3$], in which fac-[Ir(ppy)$_3$] was synthesized by reacting [Ir(acac)$_3$] with 2-phenylpyridine (Hppy) (about 3-3.5 equivalents) in an organic solvent by heating under reflux of glycerol. After using a silica-gel chromatographic column, fac-[Ir(ppy)$_3$] can be obtained in a yield of 45-60%. In addition, mer-[Ir(ppy)$_3$] displays similar luminescent behavior to that of fac-[Ir(ppy)$_3$] and can also be used as a phosphorescent dopant in an emissive layer of an OLED. Tamayo et al. (Tamayo et al., 2003) published synthesis of mer-[Ir(ppy)$_3$], in which mer-[Ir(ppy)$_3$] was synthesized by reacting [Ir$_2$(ppy)$_4$Cl$_2$] with K$_2$CO$_3$ (5-10 equivalents) and 2-phenylpyridine (Hppy) (about 2-2.5 equivalents) in an organic solvent by heating under reflux of glycerol. After using a silica-gel chromatographic column, mer-[Ir(ppy))] can be obtained in a yield of 68-80%.

Therefore, it is desirable to provide easily operated synthetic processes for preparing luminescent iridium complexes, fac-[Ir(ppy)$_3$] and mer-[Ir(ppy)$_3$], in a satisfactory yield better than 85% without using a chromatographic column for purification.

SUMMARY OF THE INVENTION

The object of the present invention is to provide novel synthetic processes for selectively and rapidly preparing iridium complexes in which water is used as a reaction solvent. Unlike conventional synthesis, no organic solvent is used for the novel synthesis provided by the present invention. Additionally, the novel synthesis provided by the present invention is advantageous in easy preparation of only one of two isomeric products and high yields. Chromatographic separation of any one pure isomer is hence not needed.

To achieve the object, the present invention provides a novel synthetic process for preparing a compound represented by the following formula (II),

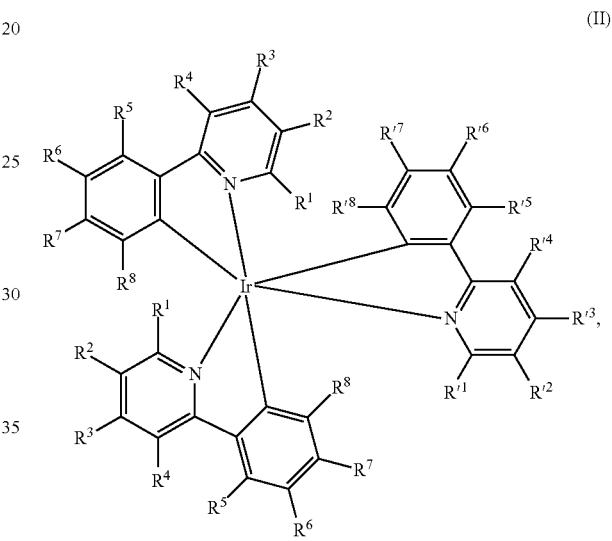

(II)

including a step of reacting a compound of the following formula (I), and a compound of the following formula (III) in water,

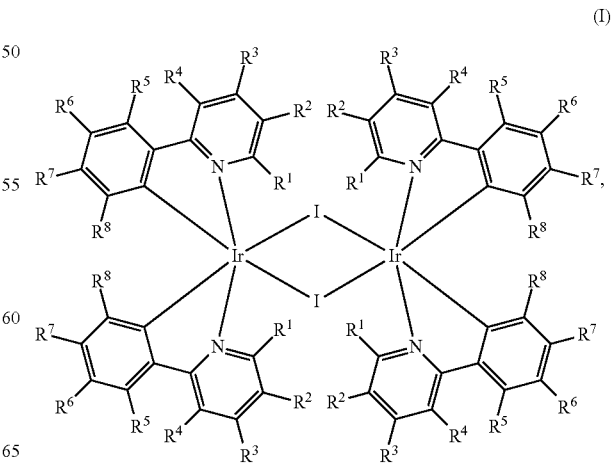

(I)

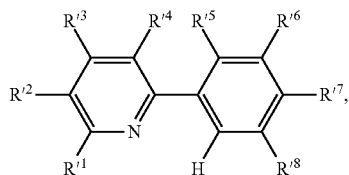

(III)

wherein each of $R^1$, $R^2$, $R^3$, $R^4$, $R^5$, $R^6$, $R^7 R^8$, $R'^1$, $R'^2$, $R'^3$, $R'^4$, $R'^5$, $R'^6$, $R'^7$, and $R'^8$, independently, is hydrogen, deuterium, alkyl, alkenyl, alkynyl, halogen, alkoxy, alkenoxy, alkynoxy, haloalkyl, haloalkenyl, haloalkynyl, cycloalkyl, cycloalkenyl or aryl; or $R^x$ and $R^{x+1}$ taken together is alkylene, alkenylene, haloalkylene or haloalkenylene, x being an integer of 1 to 7; or $R^{y}$ and $R^{y+1}$ taken together is alkylene, alkenylene, haloalkylene or haloalkenylene, y being an integer of 1 to 7.

Accordingly, the present invention can selectively synthesize the one of two luminescent iridium complexes of the formula (II) by the reaction between the precursor of the formula (I) and the compound of the formula (III) in water and the obtained product of the formula (II) is either a meridional isomer represented by the following formulas (IV) or a facial isomer represented by the following formula (V) by controlling the reaction temperature, (IV)

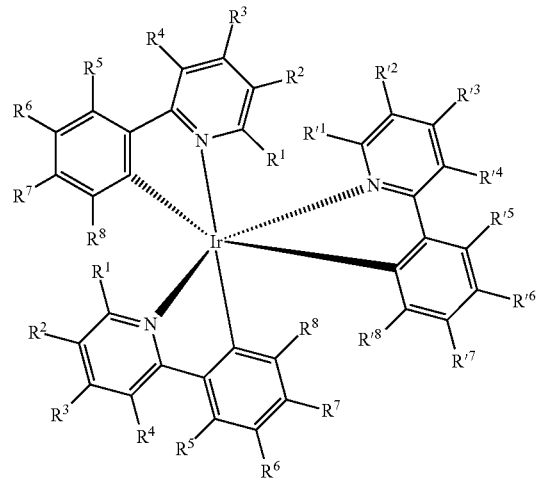

(V)

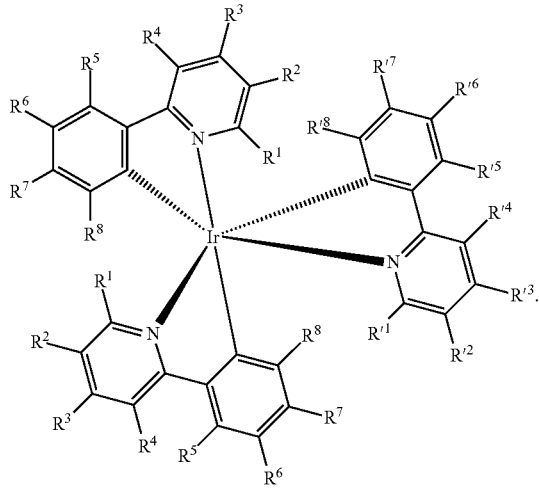

The present invention further provides a process for preparing the precursor of the formula (I), (I)

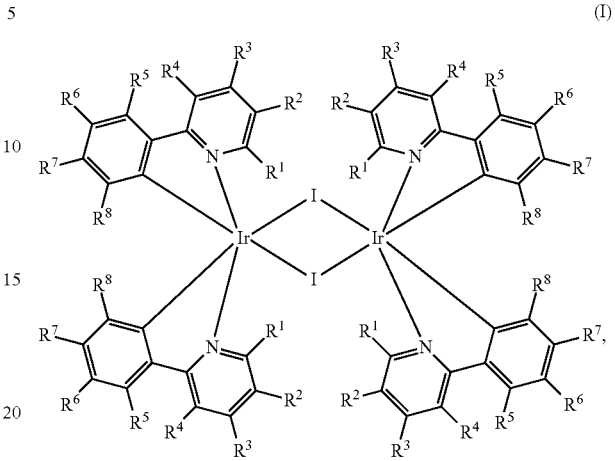

including a step of reacting $IrCl_3$ or $M_3IrCl_6$ with MI and a compound of the following formula (VI) in water, or reacting a compound of the following formula (VII) with MI in water, (VII)

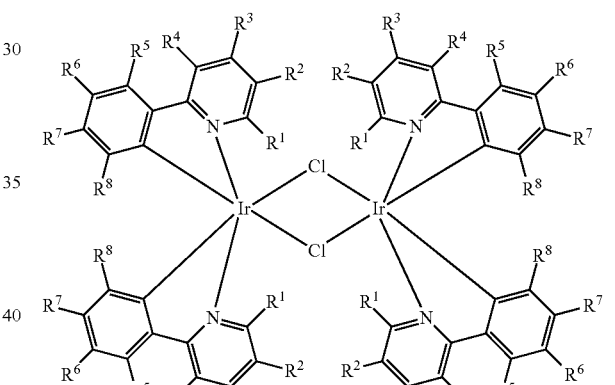

(VI)

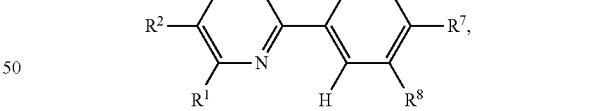

wherein
M is Li, Na or K; and
each of $R^1$, $R^2$, $R^3$, $R^4$, $R^5$, $R^6$, $R^7$ and $R^8$, independently, is hydrogen, deuterium, halogen, alkyl, alkenyl, alkynyl, alkoxy, alkenoxy, alkynoxy, cycloalkyl, cycloalkenyl or aryl; or $R^x$ and $R^{x+1}$ taken together is alkylene alkenylene, haloalkylene or haloalkenylene, x being an integer of 1 to 7.

Accordingly, the present invention can synthesize the precursor of the formula (I) in water and the precursor can be used as a starting material for a next step to synthesize the above-mentioned luminescent iridium complex of the formula (II), as a two-step synthetic process for preparing luminescent iridium complexes.

In addition, the present invention further provides another novel synthetic process for selectively preparing a compound represented by the following formula (VIII), (VIII)

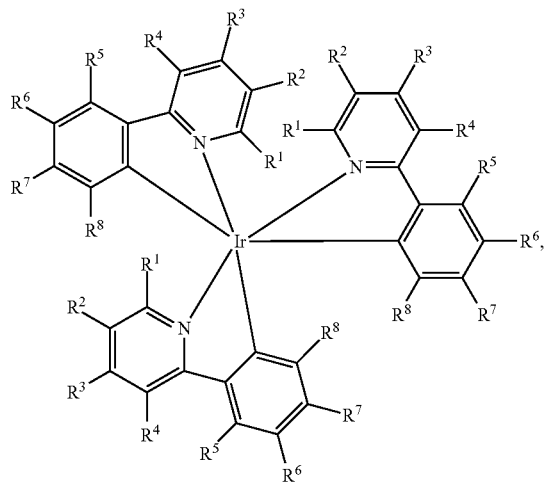

including a step of reacting IrCl$_3$ or M$_3$IrCl$_6$ with a base and a compound of the following formula (VI) in water, (VI)

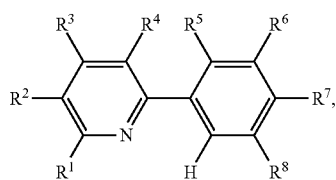

wherein
M is Li, Na or K; and
each of R$^1$, R$^2$, R$^3$, R$^4$, R$^5$, R$^6$, R$^7$ and R$^8$, independently, is hydrogen, deuterium, alkyl, alkenyl, alkynyl, halogen, alkoxy, alkenoxy, alkynoxy, haloalkyl, haloalkenyl, haloalkynyl, cycloalkyl, cycloalkenyl or aryl; or R$^x$ and R$^{x+1}$ taken together is alkylene, alkenylene, haloalkylene or haloalkenylene, x being an integer of 1 to 7.

Accordingly, the present invention can selectively synthesize any one of two luminescent iridium complexes of the formula (VIII) in water by a one-step process and the obtained product of the formula (VIII) is either a meridional isomer represented by the following formula (IX) or a facial isomer represented by the following formula (X), by controlling the amount of the base relative to that of IrCl$_3$ or M$_3$IrCl$_6$, (IX)

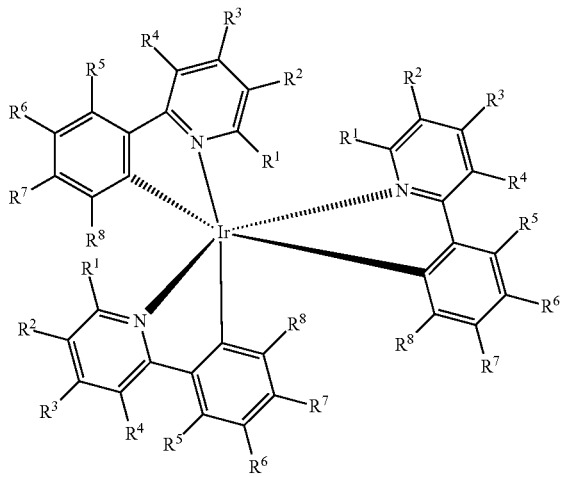

-continued (X)

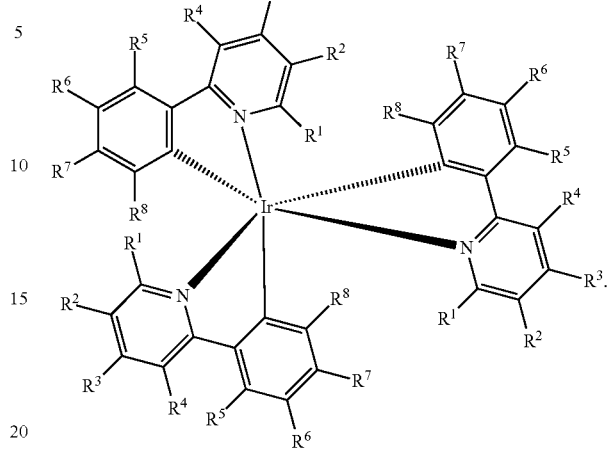

In the present invention, the base may be any organic base or any inorganic base.

In the present invention, the term "alkyl" refers to a straight or branched hydrocarbon. Examples of alkyl include, but are not limited to, methyl, ethyl, n-propyl, i-propyl, n-butyl, i-butyl, and t-butyl.

In the present invention, the term "haloalkyl" refers to alkyl substituted by one or more halogen atoms. Examples of haloalkyl include, but are not limited to, —CF$_3$, —CBr$_3$ and —CCl$_3$.

In the present invention, the term "alkoxy" refers to —O-alkyl. Examples of alkoxy include, but are not limited to, —OCH$_3$, —OCH$_2$CH$_3$ and —OCH$_2$CH$_2$CH$_3$.

In the present invention, the term "alkylene" refers to a straight or branched divalent hydrocarbon. Examples of alkylene include, but are not limited to, methylene (—CH$_2$), ethylene (—CH$_2$CH$_2$—), and i-propylene (—CHCH$_3$CH$_2$—).

In the present invention, the term "haloalkylene" refers to alkylene substituted by one or more halogen atoms. Examples of haloalkylene include, but are not limited to, —CF$_2$—, —CBr$_2$— and —CCl$_2$—.

In the present invention, the term "alkenyl" refers to a straight or branched hydrocarbon containing one or more double bonds. Examples of alkenyl include, but are not limited to, ethenyl, propenyl, allyl, and 1,4-butadienyl.

In the present invention, the term "haloalkenyl" refers to alkenyl substituted by one or more halogen atoms. Examples of haloalkenyl include, but are not limited to, —CH$_2$=CF$_2$, —CH$_2$=CBr$_2$ and —CH$_2$=CCl$_2$.

In the present invention, the term "alkenoxy" refers to O-alkenyl. Examples of alkenoxy include, but are not limited to, —OCH$_2$CH=CH$_2$, —OCH$_2$CH$_2$CH=CH$_2$ and —OCH$_2$CH$_2$CH$_2$CH=CH$_2$.

In the present invention, the term "alkenylene" refers to a straight or branched divalent hydrocarbon containing one or more double bonds. Examples of alkenylene include, but are not limited to, vinylene, and propenylene.

In the present invention, the term "halo alkenylene" refers to alkenylene substituted by one or more halogen atoms. Examples of haloalkenylene include, but are not limited to, —CH$_2$=CF—, —CH$_2$=CBr— and —CH$_2$=CCl—.

In the present invention, the term "alkynyl" refers to a straight or branched hydrocarbon containing one or more triple bonds. Examples of alkynyl include, but are not limited to, ethynyl, propynyl and butynyl.

In the present invention, the term "haloalkynyl" refers to alkynyl substituted by one or more halogen atoms. Examples of haloalkynyl include, but are not limited to, —C≡CF, —C≡CBr and —C≡CCl.

In the present invention, the term "alkynoxy" refers to O-alkynyl. Examples of alkenoxy include, but are not limited to, —OCH$_2$C≡CH, —OCH$_2$CH$_2$C≡CH and —OCH$_2$CH$_2$CH$_2$C≡CH.

In the present invention, the term "cycloalkyl" refers to a saturated hydrocarbon ring system, which may be a 5-carbon monocyclic, 10-carbon bicyclic, 14-carbon tricyclic ring system. Examples of cycloalkyl include, but are not limited to, cyclopropyl, cyclobutyl, cyclopentyl, cycloheptyl, and cyclooctyl.

In the present invention, the term "cycloalkenyl" refers to a non-aromatic hydrocarbon ring system containing one or more double bonds, which may be a 5-carbon monocyclic, 10-carbon bicyclic, 14-carbon tricyclic ring system. Examples of cycloalkenyl include, but are not limited to, cyclopentenyl and cycloheptenyl.

In the present invention, the term "aryl" refers to an aromatic ring system, which may be a 6-carbon monocyclic, 10-carbon bicyclic, 14-carbon tricyclic aromatic ring system. Examples of aryl groups include, but are not limited to, phenyl, naphthyl, and anthracenyl.

The above-mentioned alkyl, alkenyl, alkynyl, alkoxy, alkenoxy, alkynoxy, haloalkyl, haloalkenyl, haloalkynyl, cycloalkyl, cycloalkenyl, aryl, alkylene, alkenylene, haloalkylene and haloalkenylene include both substituted and unsubstituted moieties. The term "substituted" refers to one or more substituents (which may be the same or different), each replacing a hydrogen atom.

Examples of substituents for alkyl, haloalkyl, alkylene and haloalkylene include, but are not limited to, hydroxyl, amino, alkylamino, arylamino, dialkylamino, diarylamino, cyano, nitro, mercapto, carbonyl, carbamido, carbamyl, carboxyl, thiocyanato, sulfoamido, alkoxy, alkenoxy, alkynoxy, aryl, heteroaryl, cycloalkyl, cycloalkenyl, heterocycloalkyl, heterocycloalkenyl, CO$_2$-alkyl and CO$_2$-alkenyl.

Examples of substituents for alkenyl, haloalkenyl, alkenylene, and haloalkenylene include, but are not limited to, hydroxyl, amino, alkylamino, arylamino, dialkylamino, diarylamino, cyano, nitro, mercapto, carbonyl, carbamido, carbamyl, carboxyl, thiocyanato, sulfoamido, alkynyl, alkoxy, alkenoxy, alkynoxy, aryl, heteroaryl, cycloalkyl, cycloalkenyl, heterocycloalkyl, heterocycloalkenyl, CO$_2$-alkyl and CO$_2$-alkenyl.

Examples of substituents for alkynyl and haloalkynyl include, but are not limited to, hydroxyl, amino, alkylamino, arylamino, dialkylamino, diarylamino, cyano, nitro, mercapto, carbonyl, carbamido, carbamyl, carboxyl, thiocyanato, sulfoamido, alkenyl, alkoxy, alkenoxy, alkynoxy, aryl, heteroaryl, cycloalkyl, cycloalkenyl, heterocycloalkyl, heterocycloalkenyl, CO$_2$-alkyl and CO$_2$-alkenyl.

Examples of substituents for alkoxy include, but are not limited to, halogen (such as F, Cl, Br or I), hydroxyl, amino, alkylamino, arylamino, dialkylamino, diarylamino, cyano, nitro, mercapto, carbonyl, carbamido, carbamyl, carboxyl, thiocyanato, sulfoamido, alkoxy, alkenoxy, alkynoxy haloalkyl, haloalkenyl, haloalkynyl, aryl, heteroaryl, cycloalkyl, cycloalkenyl, heterocycloalkyl, heterocycloalkenyl, CO$_2$-alkyl and CO$_2$-alkenyl.

Examples of substituents for alkenoxy, include, but are not limited to, halogen (such as F, Cl, Br or I), hydroxyl, amino, alkylamino, arylamino, dialkylamino, diarylamino, cyano, nitro, mercapto, carbonyl, carbamido, carbamyl, carboxyl, thiocyanato, sulfoamido, alkynyl, alkoxy, alkenoxy, alkynoxy haloalkyl, haloalkenyl, haloalkynyl, aryl, heteroaryl, cycloalkyl, cycloalkenyl, heterocycloalkyl, heterocycloalkenyl, CO$_2$-alkyl and CO$_2$-alkenyl.

Examples of substituents for alkynoxy, include, but are not limited to, halogen (such as F, Cl, Br or I), hydroxyl, amino, alkylamino, arylamino, dialkylamino, diarylamino, cyano, nitro, mercapto, carbonyl, carbamido, carbamyl, carboxyl, thiocyanato, sulfoamido, alkenyl, alkoxy, alkenoxy, alkynoxy haloalkyl, haloalkenyl, haloalkynyl, aryl, heteroaryl, cycloalkyl, cycloalkenyl, heterocycloalkyl, heterocycloalkenyl, CO$_2$-alkyl and CO$_2$-alkenyl.

Examples of substituents for cycloalkyl, cycloalkenyl and aryl include, but are not limited to, alkyl, alkenyl, alkynyl, halogen (such as F, Cl, Br or I), hydroxyl, amino, alkylamino, arylamino, dialkylamino, diarylamino, cyano, nitro, mercapto, carbonyl, carbamido, carbamyl, carboxyl, thiocyanato, sulfoamido, alkoxy, alkenoxy, alkynoxy, haloalkyl, haloalkenyl, haloalkynyl, aryl, heteroaryl, cycloalkyl, cycloalkenyl, heterocycloalkyl, heterocycloalkenyl, CO$_2$-alkyl and CO$_2$-alkenyl.

Regarding the formulas (I), (II), (III), (IV), (V), (VI), (VII), (VIII), (IX) and (X), preferably, each of $R^1$, $R^2$, $R^3$, $R^4$, $R^5$, $R^6$, $R^7$, $R^8$, $R^{t1}$, $R^{t2}$, $R^{t3}$, $R^{t4}$, $R^{t5}$, $R^{t6}$, $R^{t7}$ and $R^{t8}$, independently, is hydrogen, deuterium, $C_{1-30}$ alkyl, $C_{2-30}$ alkenyl, $C_{2-30}$ alkynyl, halogen, $C_{1-30}$ alkoxy, $C_{2-30}$ alkenoxy, $C_{2-30}$ alkynoxy, $C_{1-30}$ haloalkyl, $C_{2-30}$ haloalkenyl, $C_{2-30}$ haloalkynyl, $C_{5-14}$ cycloalkyl, $C_{5-14}$ cycloalkenyl or $C_{6-14}$ aryl; or $R^x$ and $R^{x+1}$ taken together is $C_{3-12}$ alkylene, $C_{3-12}$ alkenylene, $C_{3-12}$ haloalkylene or $C_{3-12}$ haloalkenylene, x being an integer of 1 to 3 or 5 to 7; or $R^4$ and $R^5$ taken together is $C_{1-10}$ alkylene, $C_{2-10}$ alkenylene, $C_{1-10}$ haloalkylene or $C_{2-10}$ haloalkenylene; or $R^{ty}$ and $R^{ty+1}$ taken together is $C_{3-12}$ alkylene, $C_{3-12}$ alkenylene, $C_{3-12}$ haloalkylene or $C_{3-12}$ haloalkenylene, y being an integer of 1 to 3 or 5 to 7; or $R^{t4}$ and $R^{t5}$ taken together is $C_{1-10}$ alkylene, $C_{2-10}$ alkenylene, haloalkylene or $C_{2-10}$ haloalkenylene.

Regarding the formulas (I), (II), (III), (IV), (V), (VI), (VII), (VIII), (IX) and (X), more preferably, each of $R^1$, $R^2$, $R^3$, $R^4$, $R^5$, $R^6$, $R^7$, $R^8$, $R^{t1}$, $R^{t2}$, $R^{t3}$, $R^{t4}$, $R^{t5}$, $R^{t6}$, $R^{t7}$ and $R^{t8}$, independently, is hydrogen, deuterium, $C_{1-10}$ alkyl, $C_{2-10}$ alkenyl, $C_{2-10}$ alkynyl, halogen, $C_{1-10}$ alkoxy, $C_{2-10}$ alkenoxy, $C_{2-10}$ alkynoxy, $C_{1-10}$ haloalkyl, $C_{2-10}$ haloalkenyl, $C_{2-10}$ haloalkynyl, $C_{5-10}$ cycloalkyl, $C_{5-10}$ cycloalkenyl or $C_{6-10}$ aryl; or $R^x$ and $R^{x+1}$ taken together is $C_{3-8}$ alkylene, $C_{3-8}$ alkenylene, $C_{3-8}$ haloalkylene or $C_{3-8}$ haloalkenylene, x being an integer of 1 to 3 or 5 to 7; or $R^4$ and $R^5$ taken together is $C_{1-6}$ alkylene, $C_{2-6}$ alkenylene, $C_{1-6}$ haloalkylene or $C_{2-6}$ haloalkenylene; or $R^{ty}$ and $R^{ty+1}$ taken together is $C_{3-8}$ alkylene, $C_{3-8}$ alkenylene, $C_{3-8}$ haloalkylene or $C_{3-8}$ haloalkenylene, y being an integer of 1 to 3 or 5 to 7; or $R^{t4}$ and $R^{t5}$ taken together is $C_{1-6}$ alkylene, $C_{2-6}$ alkenylene, $C_{1-6}$ haloalkylene or $C_{2-6}$ haloalkenylene.

Regarding the formulas (I), (II), (III), (IV), (V), (VI), (VII), (VIII), (IX) and (X), most preferably, each of $R^1$, $R^2$, $R^3$, $R^4$, $R^5$, $R^6$, $R^7$, $R^8$, $R^{t1}$, $R^{t2}$, $R^{t3}$, $R^{t4}$, $R^{t5}$, $R^{t6}$, $R^{t7}$ and $R^{t8}$, independently, is hydrogen; deuterium; halogen; unsubstituted or substituted $C_{1-10}$ alkyl by one or more of $C_{1-10}$ alkoxy, $C_{2-10}$ alkenoxy and $C_{2-10}$ alkynoxy; unsubstituted or substituted $C_{2-10}$ alkenyl by one or more of $C_{2-10}$ alkynyl, $C_{1-10}$ alkoxy, $C_{2-10}$ alkenoxy and $C_{2-10}$ alkynoxy; unsubstituted or substituted $C_{2-10}$ alkynyl by one or more of $C_{2-10}$ alkenyl, $C_{1-10}$ alkoxy, $C_{2-10}$ alkenoxy and $C_{2-10}$ alkynoxy; unsubstituted or substituted $C_{1-10}$ alkoxy by one or more of halogen, $C_{1-10}$ alkoxy, $C_{2-10}$ alkenoxy and $C_{2-10}$ alkynoxy; unsubstituted or substituted $C_{2-10}$ alkenoxy by one or more of halogen, $C_{2-10}$ alkynyl, $C_{1-10}$ alkoxy, $C_{2-10}$ alkenoxy and $C_{2-10}$ alkynoxy; unsubstituted or substituted $C_{2-10}$ alkynoxy by one or more of halogen, $C_{2-10}$ alkenyl, $C_{1-10}$ alkoxy, $C_{2-10}$ alkenoxy and $C_{2-10}$ alkynoxy; unsubstituted or substituted $C_{1-10}$ haloalkyl by one or more of $C_{1-10}$ alkoxy, $C_{2-10}$ alkenoxy and $C_{2-10}$ alkynoxy; unsubstituted or substituted $C_{2-10}$ haloalkenyl by one or more of $C_{2-10}$ alkynyl, $C_{1-10}$ alkoxy, $C_{2-10}$ alkenoxy and $C_{2-10}$ alkynoxy; unsubstituted or substituted $C_{2-10}$ haloalkynyl by one or more of $C_{2-10}$ alkenyl, $C_{1-10}$ alkoxy, $C_{2-10}$ alkenoxy and $C_{2-10}$ alkynoxy; unsubstituted or substituted $C_{5-10}$ cycloalkyl by one or more of halogen, $C_{1-10}$ alkyl, $C_{2-10}$ alkenyl, $C_{2-10}$ alkynyl, $C_{1-10}$ haloalkyl, $C_{2-10}$ haloalkenyl, $C_{2-10}$ haloalkynyl, $C_{1-10}$ alkoxy, $C_{2-10}$ alkenoxy and $C_{2-10}$ alkynoxy; unsubstituted or substituted $C_{5-10}$ cycloalkenyl by one or more of halogen, $C_{1-10}$ alkyl, $C_{2-10}$ alkenyl, $C_{2-10}$ alkynyl, $C_{1-10}$ haloalkyl, $C_{2-10}$ haloalkenyl, $C_{2-10}$ haloalkynyl, $C_{1-10}$ alkoxy, $C_{2-10}$ alkenoxy and $C_{2-10}$ alkynoxy; or unsubstituted or substituted $C_{6-10}$ aryl by one or more of halogen, $C_{1-10}$ alkyl, $C_{2-10}$ alkenyl, $C_{2-10}$ alkynyl, $C_{1-10}$ haloalkyl, $C_{2-10}$ haloalkenyl, $C_{2-10}$ haloalkynyl, $C_{1-10}$ alkoxy, $C_{2-10}$ alkenoxy and $C_{2-10}$ alkynoxy; or $R^x$ and $R^{x+1}$ (x being an integer of 1 to 3 or 5 to 7) taken together is unsubstituted or substituted $C_{3-5}$ alkylene by one or more of $C_{2-10}$ alkynyl, $C_{1-10}$ alkoxy, $C_{2-10}$ alkenoxy and $C_{2-10}$ alkynoxy thus forming a 5-7 membered ring with two carbons bonded to $R^x$ and $R^{x+1}$; unsubstituted or substituted $C_{3-5}$ alkenylene by one or more of $C_{2-10}$ alkynyl, $C_{1-3}$ alkoxy, $C_{2-10}$ alkenoxy and $C_{2-10}$ alkynoxy thus forming a 5-7 membered ring with two carbons bonded to $R^x$ and $R^{x+1}$; unsubstituted or substituted $C_{3-5}$ haloalkylene by one or more of $C_{2-10}$ alkynyl, $C_{1-10}$ alkoxy, $C_{2-10}$ alkenoxy and $C_{2-10}$ alkynoxy thus forming a 5-7 membered ring with two carbons bonded to $R^x$ and $R^{x+1}$; or unsubstituted or substituted $C_{3-5}$ haloalkenylene by one or more of $C_{2-10}$ alkynyl, $C_{1-10}$ alkoxy, $C_{2-10}$ alkenoxy and $C_{2-10}$ alkynoxy thus forming a 5-7 membered ring with two carbons bonded to $R^x$ and $R^{x+1}$; or $R^4$ and $R^5$ taken together is unsubstituted or substituted $C_{1-3}$ alkylene by one or more of $C_{2-10}$ alkynyl, $C_{1-10}$ alkoxy, $C_{2-10}$ alkenoxy and $C_{2-10}$ alkynoxy thus forming a 5-7 membered ring with two carbons bonded to $R^4$ and $R^5$ and two carbons adjacent to the two carbons bonded to $R^4$ and $R^5$; unsubstituted or substituted $C_{2-3}$ alkenylene by one or more of $C_{2-10}$ alkynyl, $C_{1-10}$ alkoxy, $C_{2-10}$ alkenoxy and $C_{2-10}$ alkynoxy thus forming a 6-7 membered ring with two carbons bonded to $R^4$ and $R^5$ and two carbons adjacent to the two carbons bonded to $R^4$ and $R^5$; unsubstituted or substituted $C_{1-3}$ haloalkylene by one or more of $C_{2-10}$ alkynyl, $C_{1-10}$ alkoxy, $C_{2-10}$ alkenoxy and $C_{2-10}$ alkynoxy thus forming a 5-7 membered ring with two carbons bonded to $R^4$ and $R^5$ and two carbons adjacent to the two carbons bonded to $R^4$ and $R^5$; or unsubstituted or substituted $C_{2-3}$ haloalkenylene by one or more of $C_{2-10}$ alkynyl, $C_{1-10}$ alkoxy, $C_{2-10}$ alkenoxy and $C_{2-10}$ alkynoxy thus forming a 6-7 membered ring with two carbons bonded to $R^4$ and $R^5$ and two carbons adjacent to the two carbons bonded to $R^4$ and $R^5$; or $R^{ty}$ and $R^{ty+1}$ (y being an integer of 1 to 3 or 5 to 7) taken together is unsubstituted or substituted $C_{3-5}$ alkylene by one or more of $C_{2-10}$ alkynyl, $C_{1-10}$ alkoxy, $C_{2-10}$ alkenoxy and $C_{2-10}$ alkynoxy thus forming a 5-7 membered ring with two carbons bonded to $R^{ty}$ and $R^{ty+1}$; unsubstituted or substituted $C_{3-5}$ alkenylene by one or more of $C_{2-10}$ alkynyl, $C_{1-10}$ alkoxy, $C_{2-10}$ alkenoxy and $C_{2-10}$ alkynoxy thus forming a 5-7 membered ring with two carbons bonded to $R^{ty}$ and $R^{ty+1}$; unsubstituted or substituted $C_{3-5}$ haloalkylene by one or more of $C_{2-10}$ alkynyl, $C_{1-10}$ alkoxy, $C_{2-10}$ alkenoxy and $C_{2-10}$ alkynoxy thus forming a 5-7 membered ring with two carbons bonded to $R^{ty}$ and $R^{ty+1}$; or unsubstituted or substituted $C_{3-5}$ haloalkenylene by one or more of $C_{2-10}$ alkynyl, $C_{1-10}$ alkoxy, $C_{2-10}$ alkenoxy and $C_{2-10}$ alkynoxy thus forming a 5-7 membered ring with two carbons bonded to $R^{ty}$ and $R^{ty+1}$; or $R^{t4}$ and $R^{t5}$ taken together is unsubstituted or substituted $C_{1-3}$ alkylene by one or more of $C_{2-10}$ alkynyl, $C_{1-10}$ alkoxy, $C_{2-10}$ alkenoxy and $C_{2-10}$ alkynoxy thus forming a 5-7 membered ring with two carbons bonded to $R^{t4}$ and $R^{t5}$ and two carbons adjacent to the two carbons bonded to $R^{t4}$ and $R^{t5}$; unsubstituted or substituted $C_{2-3}$ alkenylene by one or more of $C_{2-10}$ alkynyl, $C_{1-10}$ alkoxy, $C_{2-10}$ alkenoxy and $C_{2-10}$ alkynoxy thus forming a 6-7 membered ring with two carbons bonded to $R^{t4}$ and $R^5$ and two carbons adjacent to the two carbons bonded to $R^{t4}$ and $R^{t5}$; unsubstituted or substituted $C_{1-3}$ haloalkylene by one or more of $C_{2-10}$ alkynyl, $C_{1-10}$ alkoxy, $C_{2-10}$ alkenoxy and $C_{2-10}$ alkynoxy thus forming a 5-7 membered ring with two carbons bonded to $R^{t4}$ and $R^{t5}$ and two carbons adjacent to the two carbons bonded to $R^{t4}$ and $R^{t5}$; or unsubstituted or substituted $C_{2-3}$ haloalkenylene by one or more of $C_{2-10}$ alkynyl, $C_{1-10}$ alkoxy, $C_{2-10}$ alkenoxy and $C_{2-10}$ alkynoxy thus forming a 6-7 membered ring with two carbons bonded to $R^{t4}$ and $R^{t5}$ and two carbons adjacent to the two carbons bonded to $R^{t4}$ and $R^{t5}$.

Examples of the formula (I) include, but are not limited to,

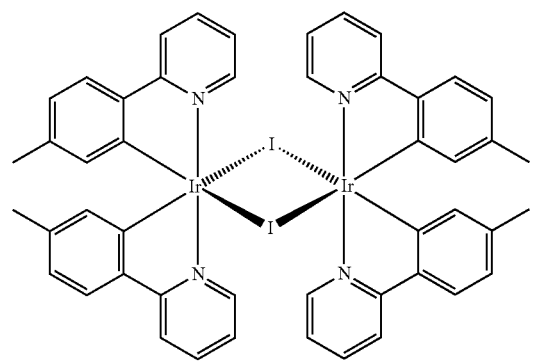

-continued
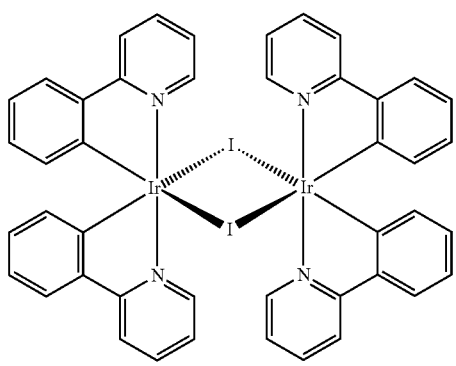
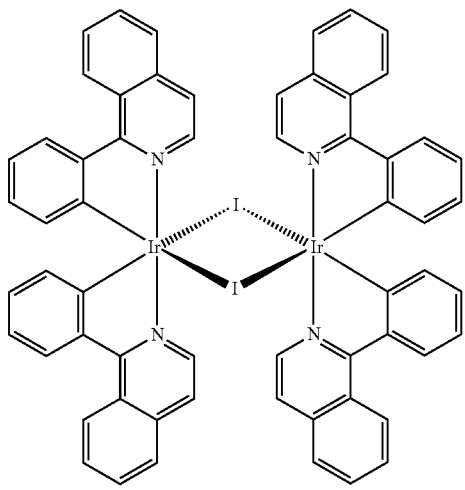
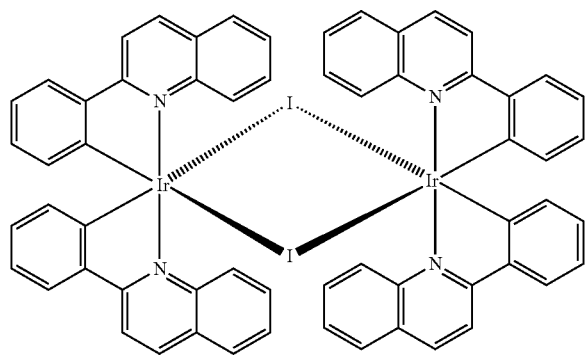
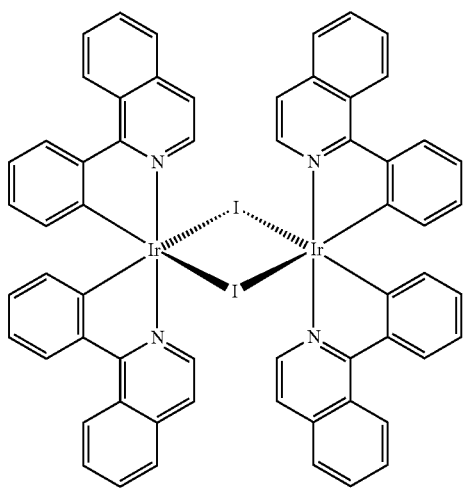

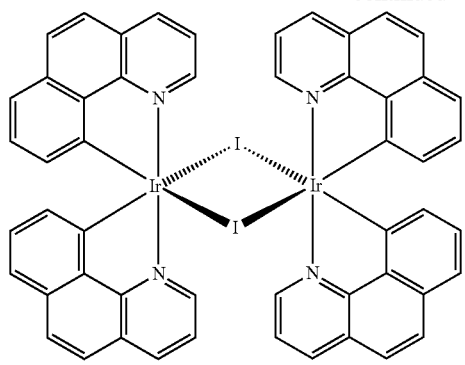
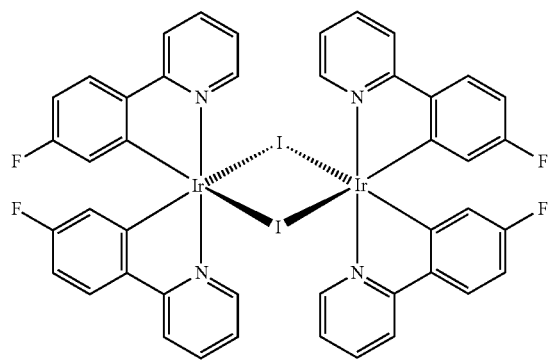
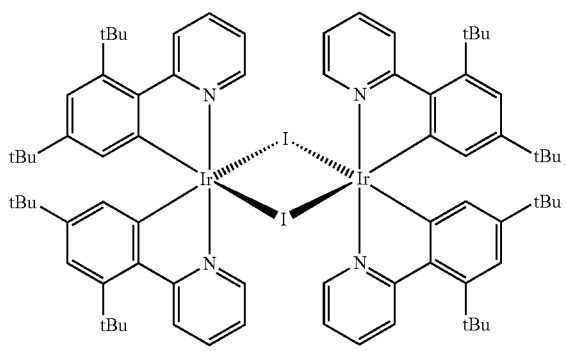
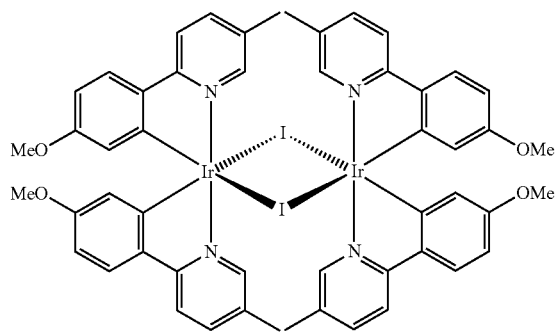

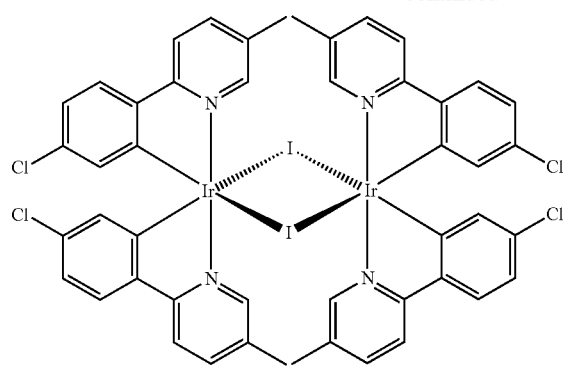
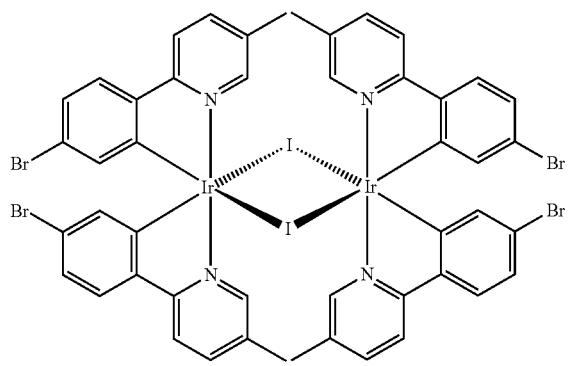
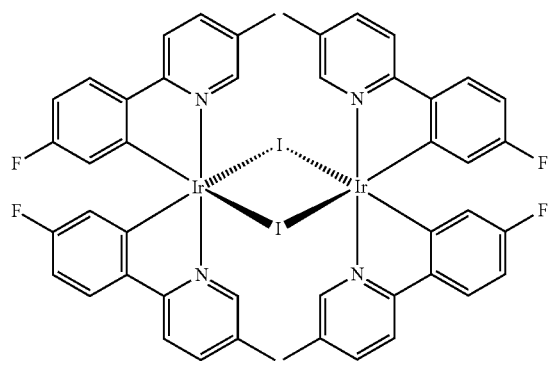
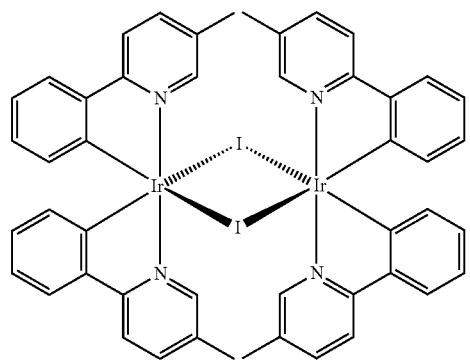

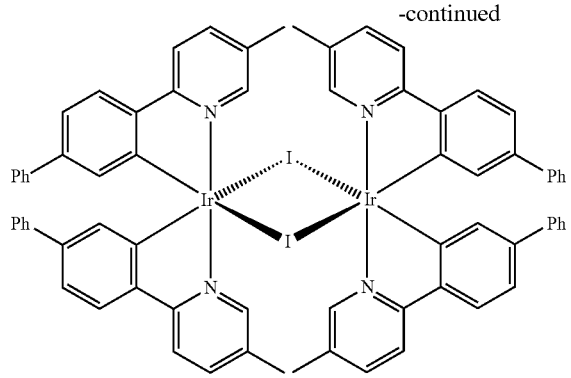
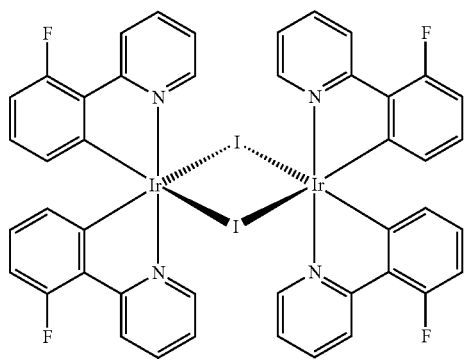
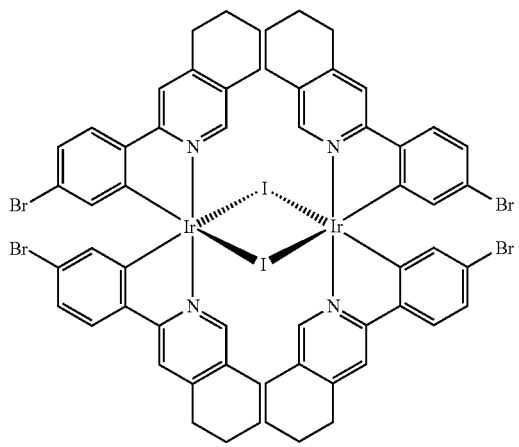
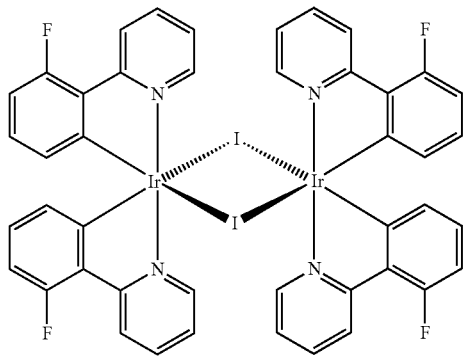

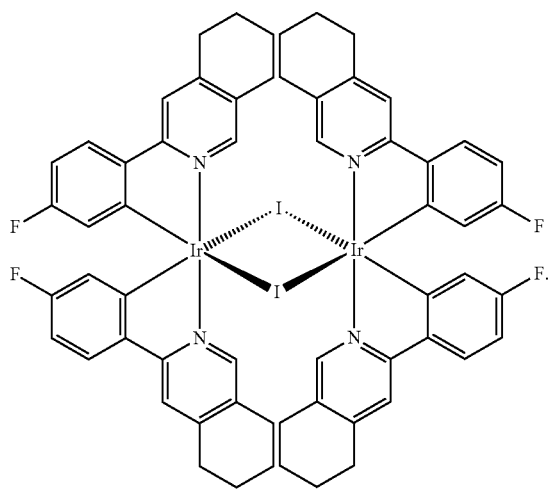
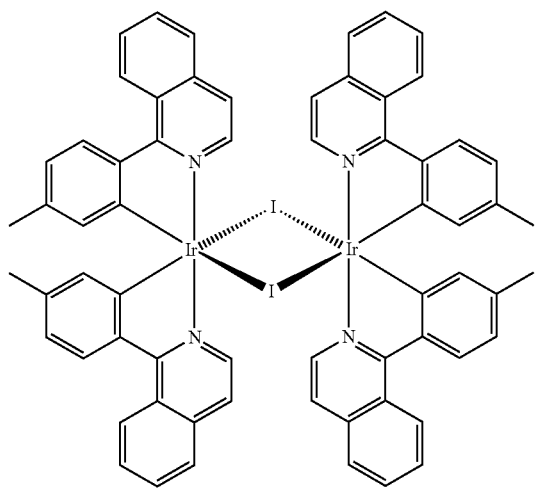
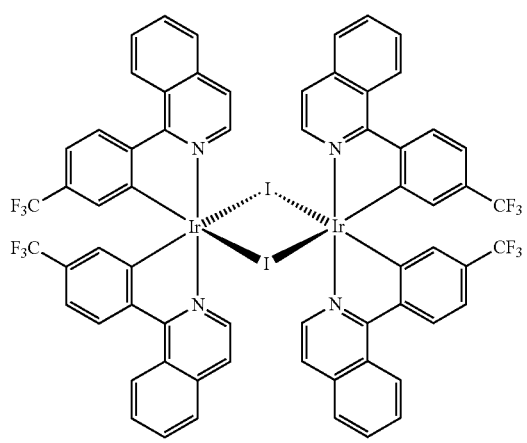

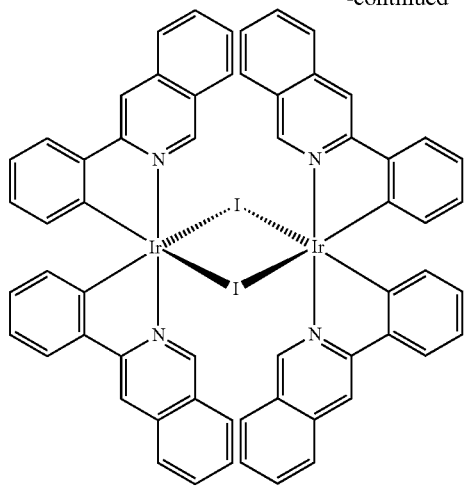
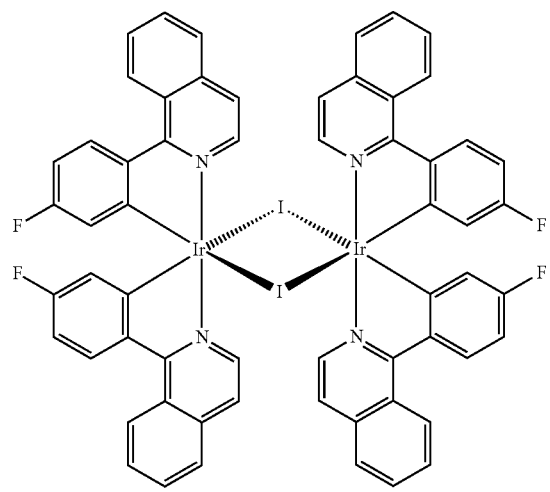
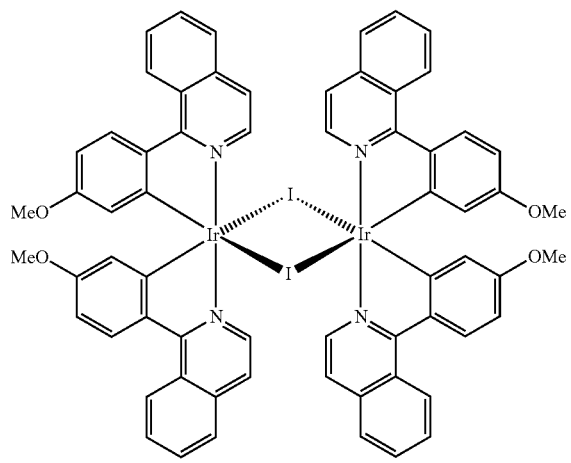

Examples of the formulas (III) and (VI) include, but are not limited to,

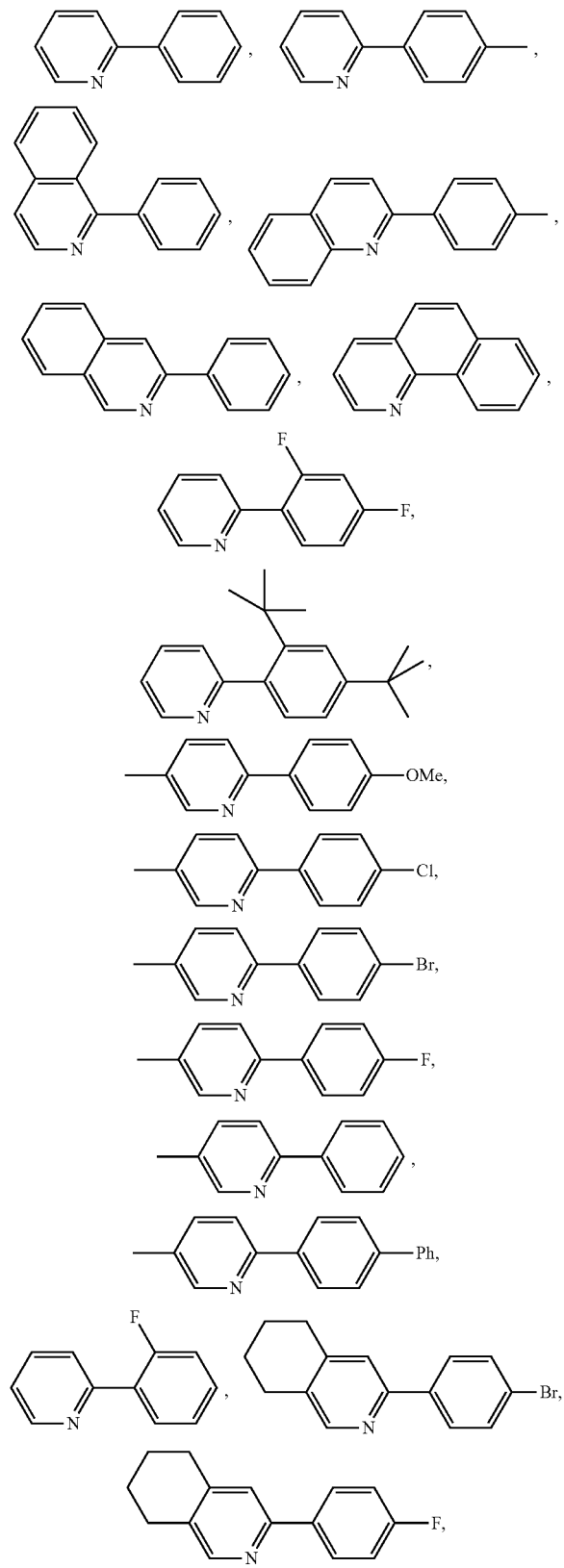

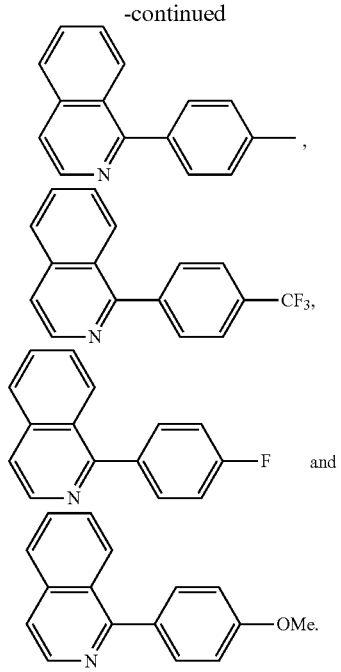

Accordingly, the present invention provides a novel one-step or two-step synthetic process for selectively preparing luminescent iridium complexes in which water is used as a reaction solvent. Unlike conventional synthesis, no organic solvent is used for the novel synthetic synthesis provided by the present invention. Additionally, the novel synthetic synthesis provided by the present invention is advantageous in selective preparation of any one of two isomeric products and high yields.

Other objects, advantages, and novel features of the invention will become more apparent from the following detailed description when taken in conjunction with the accompanying drawings.

BRIEF DESCRIPTION OF THE DRAWINGS

None

DETAILED DESCRIPTION OF THE PREFERRED EMBODIMENT

A better understanding of the present invention may be obtained in light of the following Examples which are set forth to illustrate, but are not to be construed to limit the present invention.

As a two-step synthesis, precursors of $[Ir_2(C_{11}NR_8)_4I_2]$ were first prepared from $IrCl_3, M_3IrCl_6$ or complexes of $[Ir_2(C_{11}NR_8)_4Cl_2]$ and then final luminescent iridium complexes of $[Ir(C_{11}NR_8)_2(C_{11}NR'_8)]$ were synthesized from the precursors. Herein, the prepared $[Ir(C_{11}NR_8)_2(C_{11}NR'_8)]$ is either fac-$[Ir(C_{11}NR_8)_2(C_{11}NR'_8)]$ or mer-$[Ir(C_{11}NR_8)_2(C_{11}NR'_8)]$ by controlling the reaction temperature.

Synthesis of $[Ir_2(ppy)_4I_2]$

A precursor of $[Ir_2(ppy)_4I_2]$ was prepared by reacting $IrCl_3$ or $M_3IrCl_6$ with KI and 2-phenylpyridine (Hppy), or reacting a complex of $[Ir_2(ppy)_4Cl_2]$ with KI as follows. Herein, M is one of Li, Na and K, and ppy is 2-phenylpyridyl.

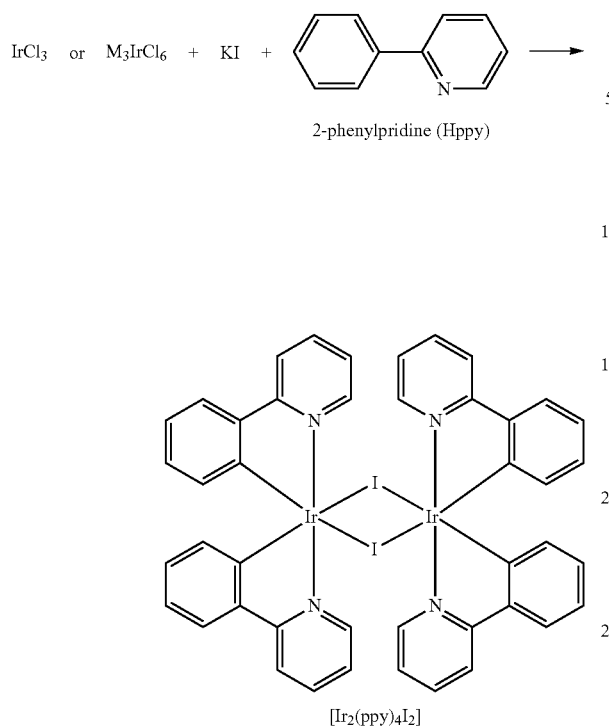

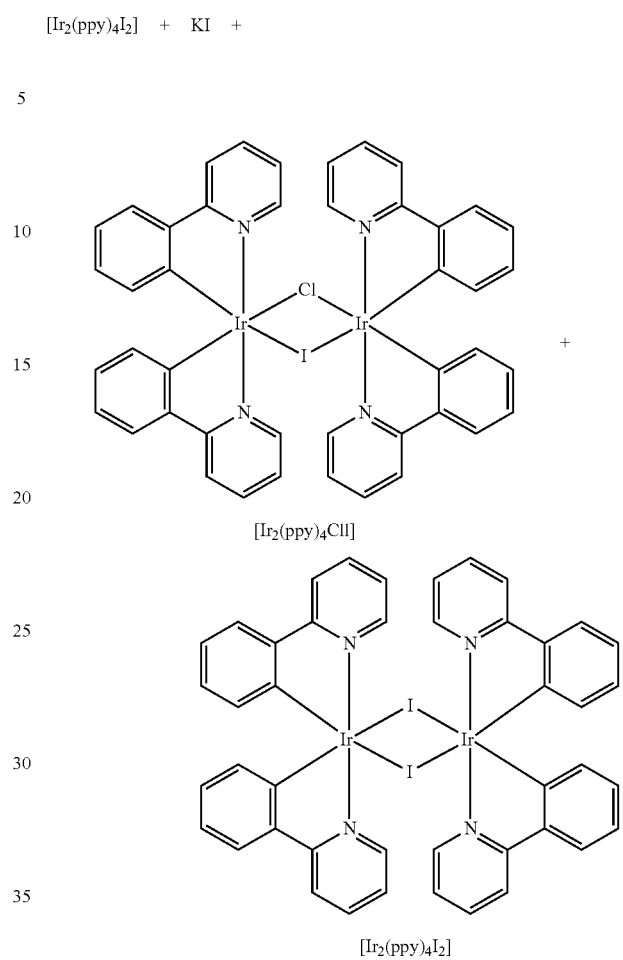

Example 1

IrCl$_3$ (0.052 g, 0.15 mmole), KI (0.125 g, 0.75 mmole) and 2-phenylpyridine (0.1 ml) were placed in a Teflon-lined autoclave, and then deionized water (10 ml) was added thereto. Subsequently, the autoclave was sealed and heated to perform reaction for 22 hours in an oven at 150° C. Finally, solids collected on a filter paper were washed with deionized water (30 ml) and recrystallized from dichloromethane/hexane to obtain a product of 0.083 g in a yield of 88%.

Example 2

An Na$_3$IrCl$_6$ aqueous solution containing Na$_3$IrCl$_6$ (0.15 mmol) and deionized water (10 ml) was placed in a Teflon-lined autoclave, and then KI (0.343 g, 2.07 mmole) and 2-phenylpyridine (0.1 ml) were added thereto. Subsequently, the autoclave was sealed and heated to perform reaction for 24 hours in an oven at 150° C. Finally, solids collected on a filter paper were washed with deionized water (30 ml) and recrystallized from dichloromethane/hexane to obtain a product of 0.086 g in a yield of 91%.

The present example also replaced the Na$_3$IrCl$_6$ aqueous solution with other suitable aqueous solutions, such as Li$_3$IrCl$_6$ aqueous solution or K$_3$IrCl$_6$ aqueous solution, to perform the above-mentioned reaction with KI and 2-phenylpyridine, thus obtaining the product of [Ir$_2$(ppy)$_4$I$_2$].

Example 3

[Ir$_2$(ppy)$_4$Cl$_2$] (0.038 g, 0.035 mmole) and KI (0.583 g, 0.35 mmole, 10 equivalents) were placed in a Teflon-lined autoclave, and then deionized water (10 ml) was added thereto. Subsequently, the autoclave was sealed and heated to perform reaction for 24 hours in an oven at 150° C. Finally, solids collected on a filter paper were washed with deionized water (30 ml) and recrystallized from dichloromethane/hexane to obtain a product mixture of [Ir$_2$(ppy)$_4$ClI] and [Ir$_2$(ppy)$_4$ I$_2$].

The present example also used KI in an amount of 20, 30 or 40 equivalents to perform the above-mentioned process, and ratios obtained for the unreacted compound, [Ir$_2$(ppy)$_4$Cl$_2$], and two products were determined from the integrals of $^1$H NMR spectra (Table 1).

TABLE 1

| KI (equivs.) | [Ir$_2$(ppy)$_4$I$_2$] | [Ir$_2$(ppy)$_4$Cl$_2$] | [Ir$_2$(ppy)$_4$ClI] |
|---|---|---|---|
| 10 | 0.279% | 0.553% | 0.168% |
| 20 | 0.784% | 0.085% | 0.131% |
| 30 | 0.188% | 0.637% | 0.175% |
| 40 | 0.045% | 0.851% | 0.104% |

By using various reactants, various products can be synthesized as follows.
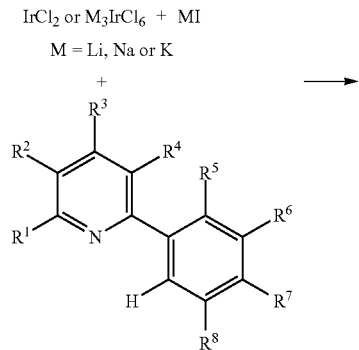
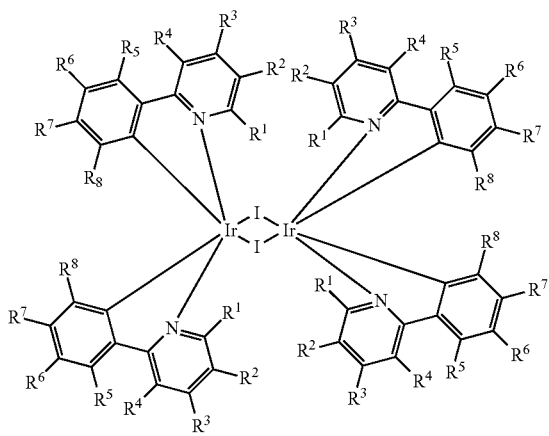
[Ir$_2$(C$_{11}$NR$_8$)$_4$I$_2$]
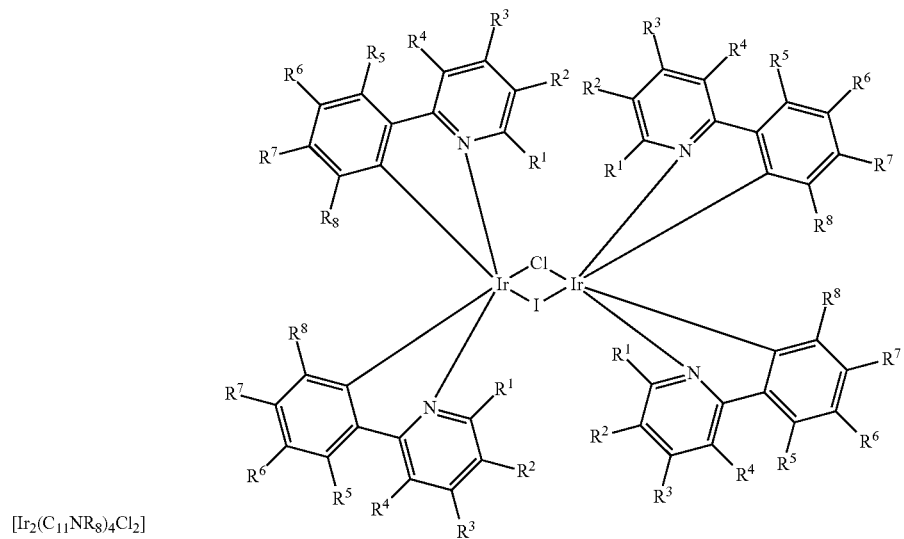
[Ir$_2$(C$_{11}$NR$_8$)$_4$Cl$_2$]

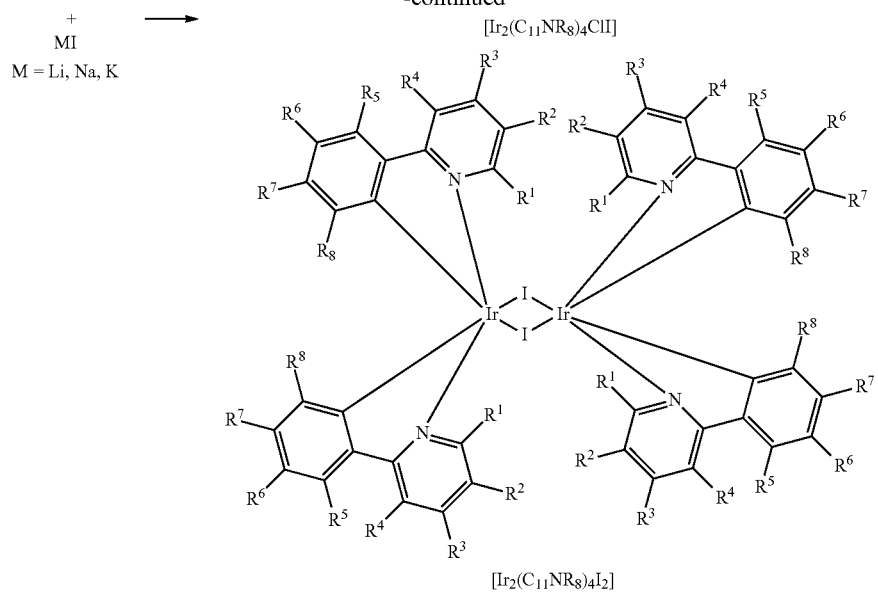

Herein, M is Li, Na or K; and each of $R^1$, $R^2$, $R^3$, $R^4$, $R^5$, $R^6$, $R^7$ and $R^8$, independently, is hydrogen, deuterium, halogen, alkyl, alkenyl, alkynyl, alkoxy, alkenoxy, alkynoxy, cycloalkyl, cycloalkenyl or aryl; or $R^x$ and $R^{x+1}$ taken together is alkylene, alkenylene, haloalkylene or haloalkenylene, x being an integer of 1 to 7.

Examples of $[Ir_2(C_{11}NR_8)_4I_2]$ include, but are not limited to,

-continued

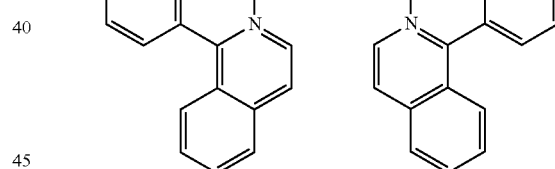

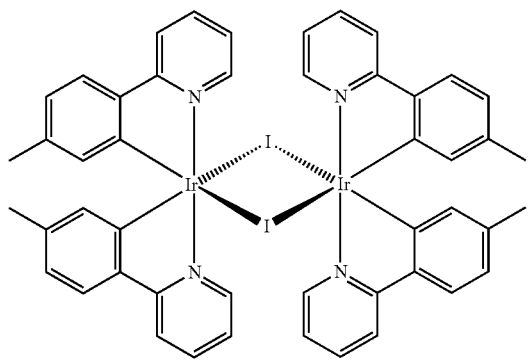

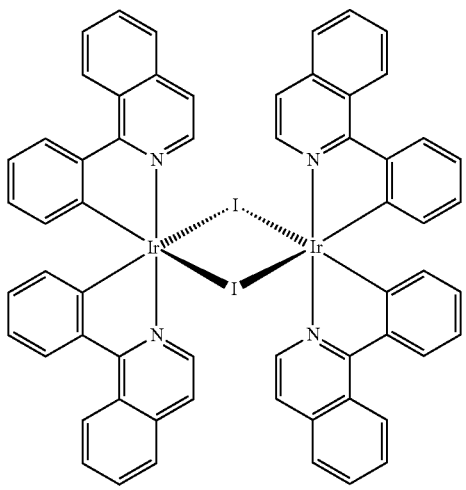

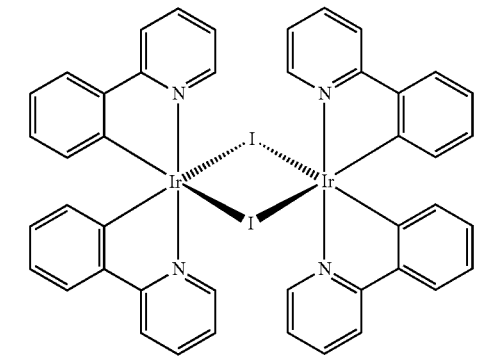

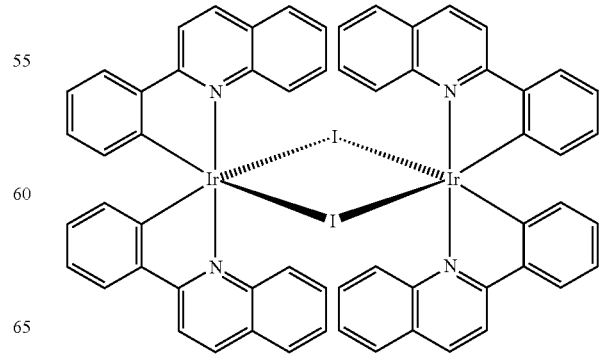

-continued
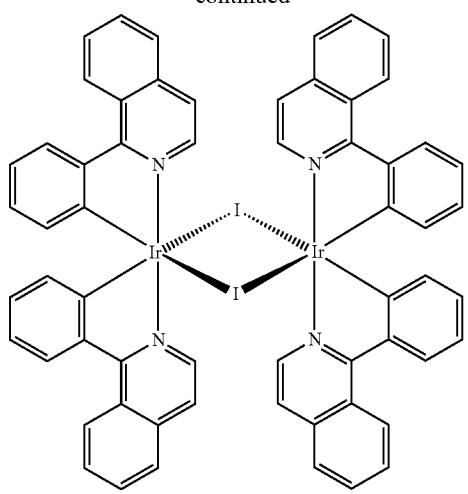
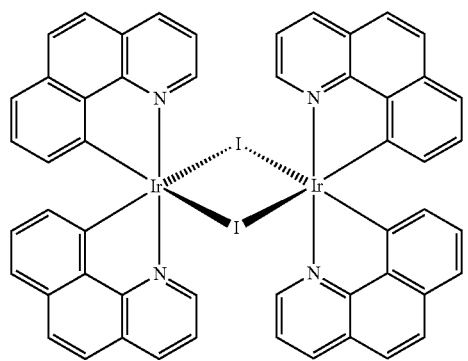
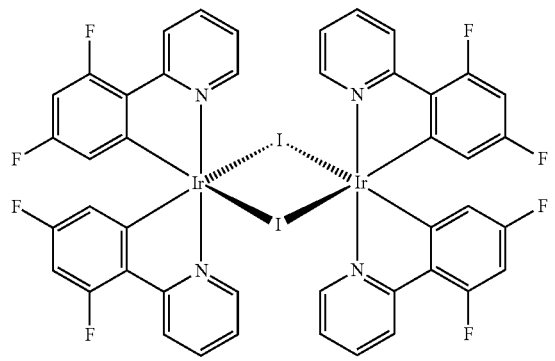
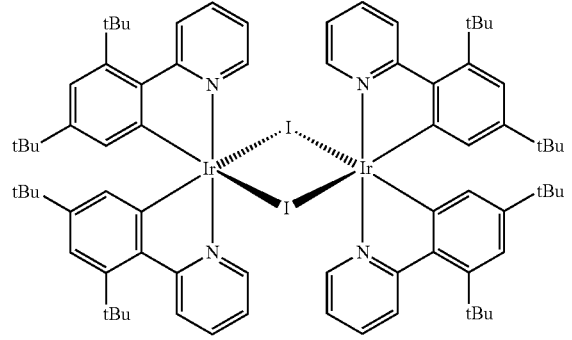
-continued
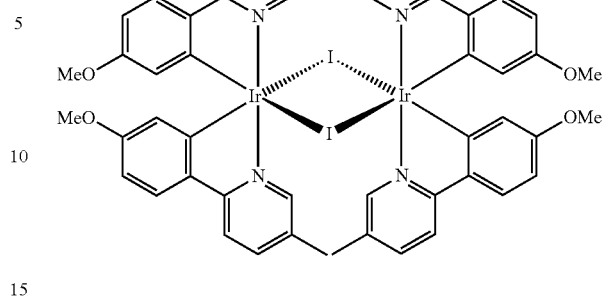
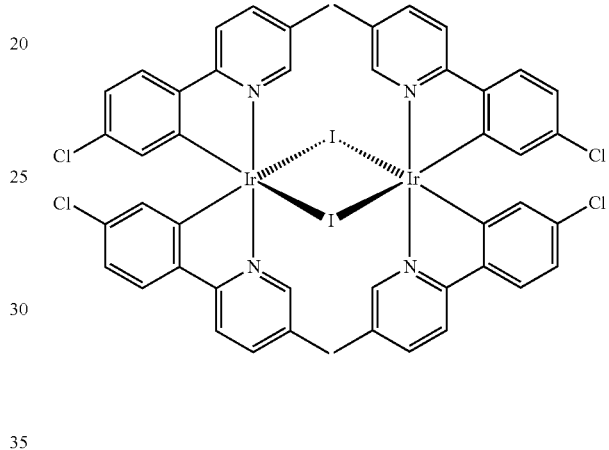
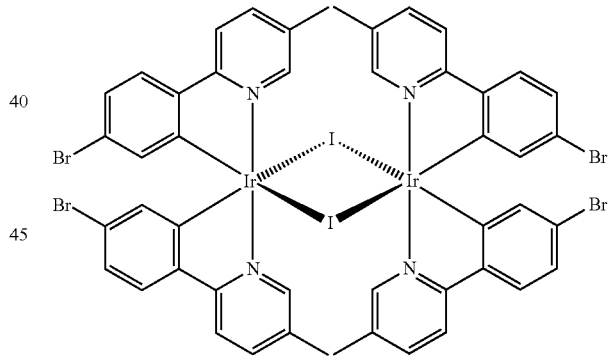
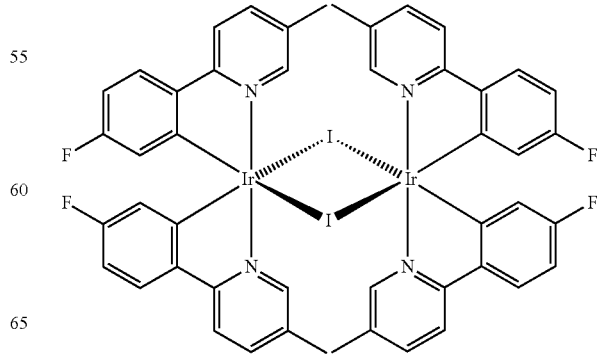

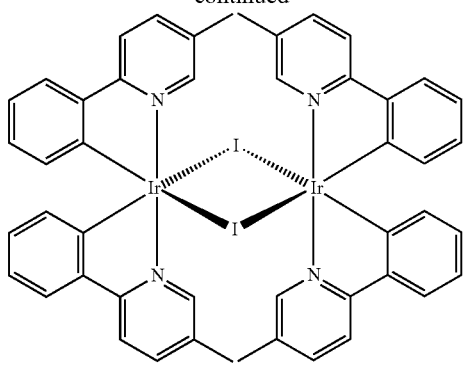
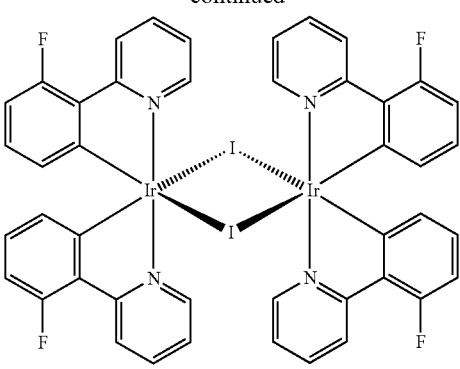
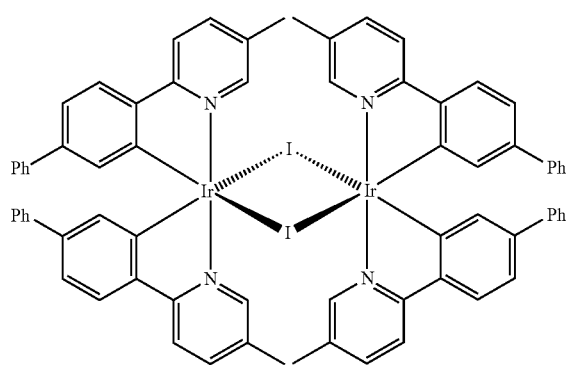
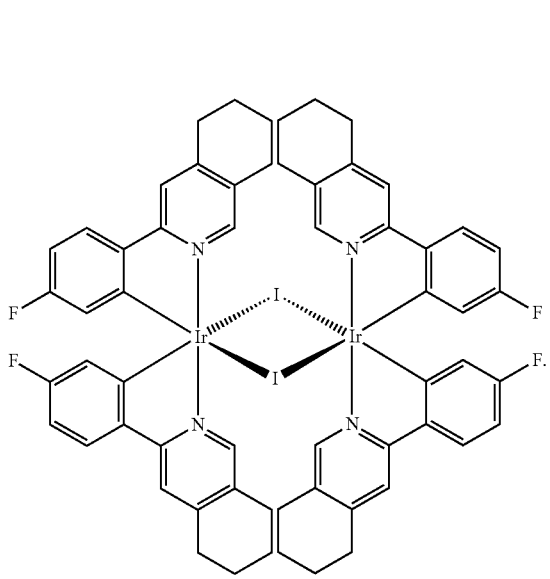
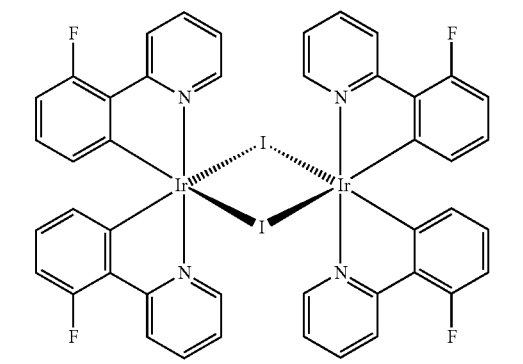
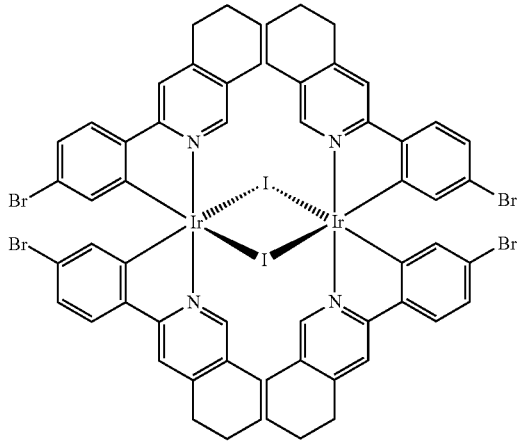
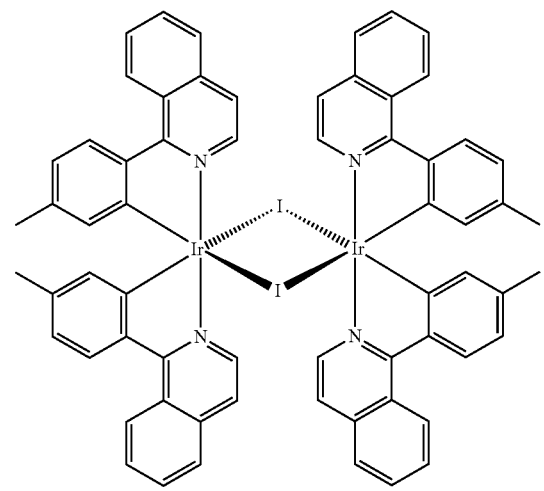

-continued

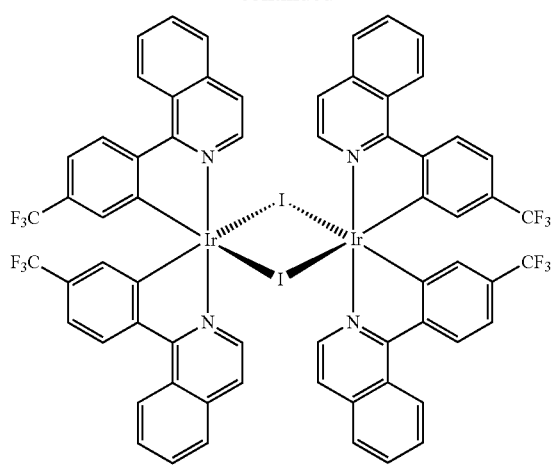

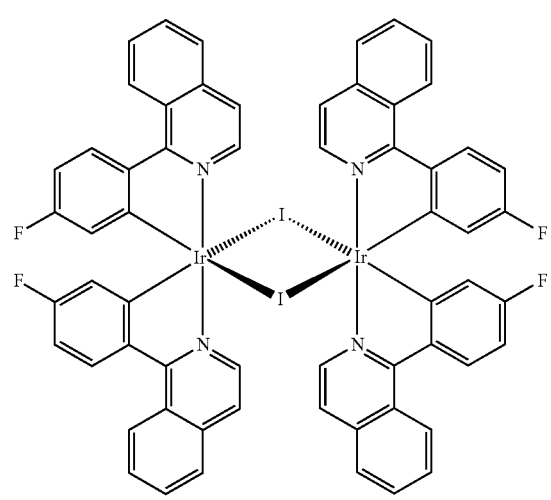

-continued

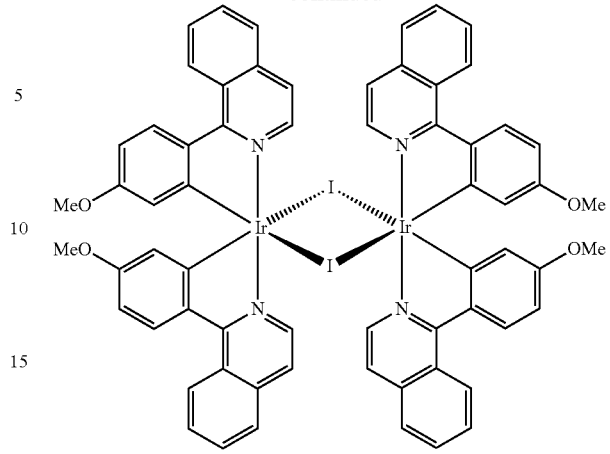

Synthesis of [Ir(ppy)₃]

A luminescent organic complex of [Ir(ppy)₃] can be obtained by reacting the precursor of [Ir₂(ppy)₄I₂], prepared by Examples 1-3 with 2-phenylpyridine. Herein, the prepared [Ir(ppy)₃] is either fac-[Ir(ppy)₃] or mer-[Ir(ppy)₃], or one of two isomers in whole or in majority.

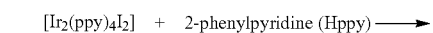

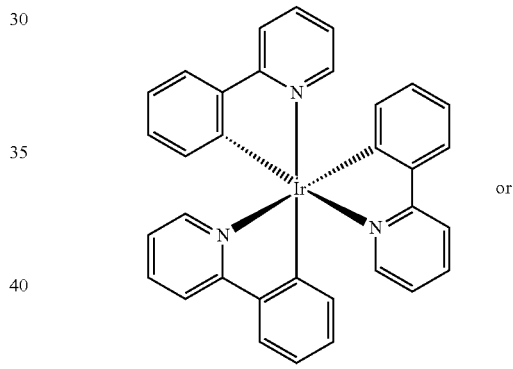

fac-[Ir(ppy)₃]

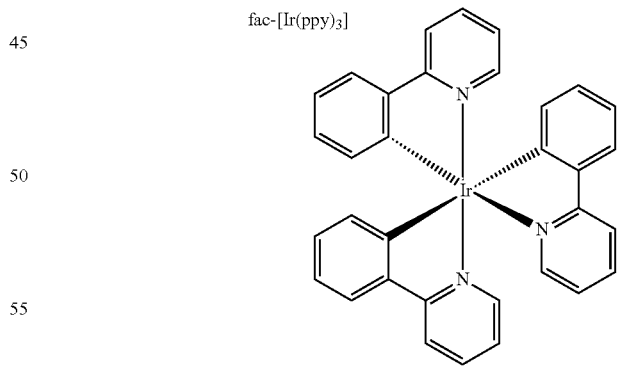

mer-[Ir(ppy)₃]

Example 4

Selective Synthesis of mer-[Ir(ppy)₃]

[Ir₂(ppy)₄I₂](0.0740 g, 0.059 mmole) and 2-phenylpyridine (0.08 ml, 0.54 mmol) were placed in a Teflon-lined autoclave, and then deionized water (10 ml) was added thereto. Subsequently, the autoclave was sealed and heated to perform reaction for 20 hours in an oven at 150° C. After cooling, solids were collected on a filter paper, washed with deionized water (50 ml) and recrystallized from dichloromethane/hexane to obtain a yellow product mer-[Ir(ppy)$_3$] of 0.0672 g in a yield of 87%.

Example 5

Selective Synthesis of fac-[Ir(ppy)$_3$]

[Ir$_2$(ppy)$_4$I$_2$] (0.0623 g, 0.050 mmole) and 2-phenylpyridine (0.08 ml, 0.54 mmol) were placed in a Teflon-lined autoclave, and then deionized water (10 ml) was added thereto. Subsequently, the autoclave was sealed and heated to perform reaction for 24 hours in an oven at 200° C. After cooling, solids were collected on a filter paper, washed with deionized water (50 ml) and recrystallized from dichloromethane/hexane to obtain a yellow product fac-[Ir(ppy)$_3$] of 0.0576 g in a yield of 88%.

Example 6

Selective Synthesis of fac-[Ir(tpy)$_3$]

[Ir$_2$(tpy)$_4$I$_2$] (0.0326 g, 0.025 mmole) and Htpy (0.0110 g, 0.06 mmole) were placed in a Teflon-lined autoclave, and then deionized water (10 ml) was added thereto. Subsequently, the autoclave was sealed and heated to perform reaction for 24 hours in an oven at 150° C. After cooling, solids were collected on a filter paper, washed with deionized water (50 ml) and recrystallized from dichloromethane/hexane to obtain a yellow product fac-[Ir(tpy)$_3$] of 0.0311 g in a yield of 89%.

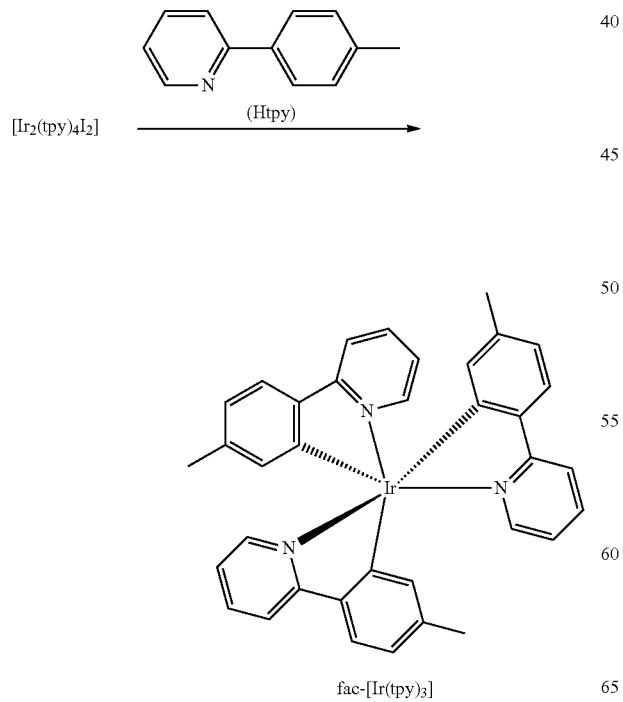

By using various reactants, various products can be synthesized as follows.

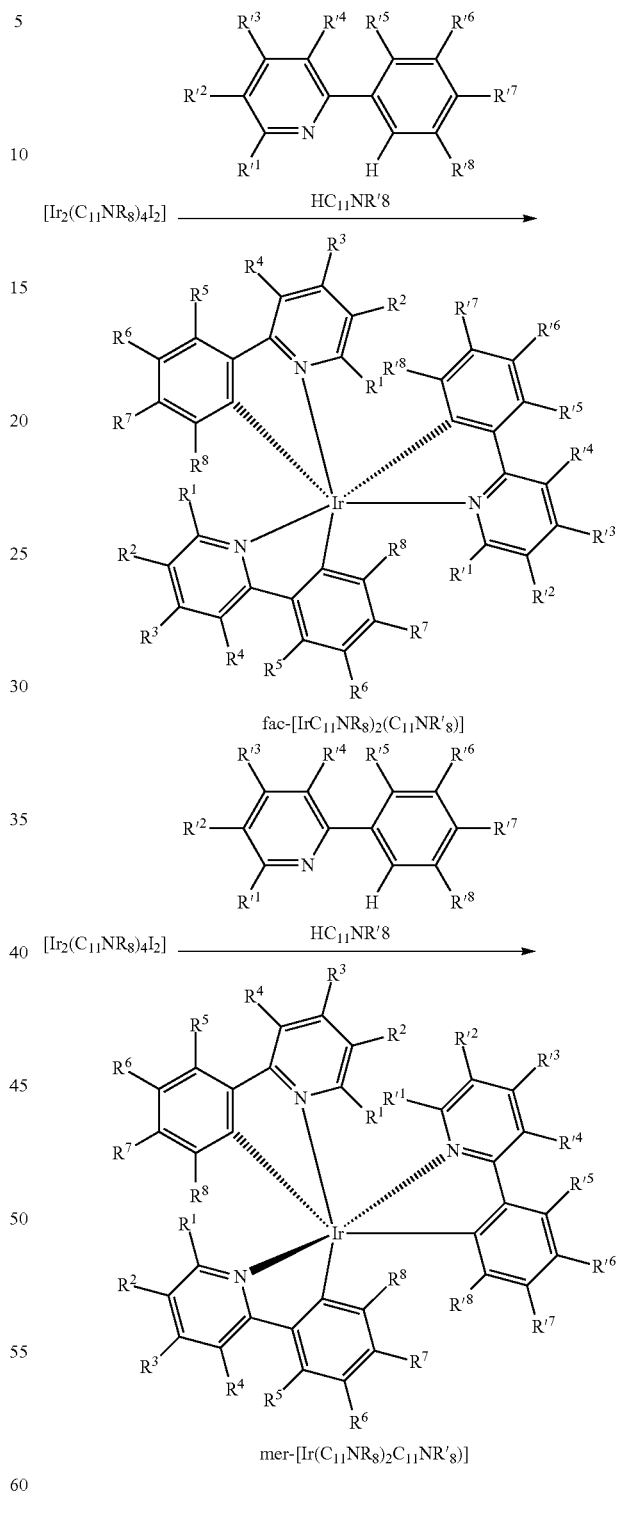

Herein, each of $R^1$, $R^2$, $R^3$, $R^4$, $R^5$, $R^6$, $R^7$, $R^8$, $R'^1$, $R'^2$, $R'^3$, $R'^4$, $R'^5$, $R'^6$, $R'^7$ and $R'^8$, independently, is hydrogen, deuterium, alkyl, alkenyl, alkynyl, halogen, alkoxy, alkenoxy, alkynoxy, haloalkyl, haloalkenyl, haloalkynyl, cycloalkyl, cycloalkenyl or aryl; or $R^x$ and $R^{x+1}$ taken together is alkylene, alkenylene, haloalkylene or haloalkenylene, x being an integer of 1 to 7; or $R^{y'}$ and $R^{y'+1}$ taken together is alkylene, alkenylene, haloalkylene or haloalkenylene, y being an integer of 1 to 7.

As an one-step synthesis, any one of the two luminescent iridium isomeric complexes of [Ir($C_{11}NR_8$)$_3$] can be selectively prepared from a complex of IrCl$_3$ or M$_3$IrCl$_6$ (M is Li, Na or K) with H$C_{11}NR_8$ in the presence of a base. Herein, the prepared [Ir($C_{11}NR_8$)$_3$] is either fac-[Ir($C_{11}NR_8$)$_3$] or mer-[Ir($C_{11}NR_8$)$_3$] by controlling the amount of the base relative to that of IrCl$_3$ or M$_3$IrCl$_6$ as follows.

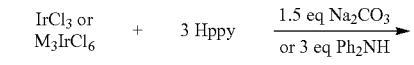

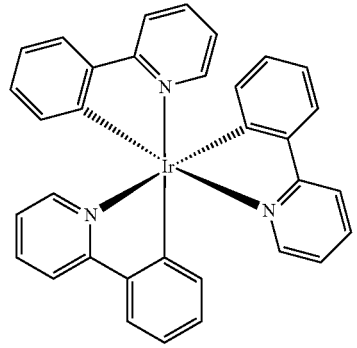

fac-[Ir(ppy)$_3$]

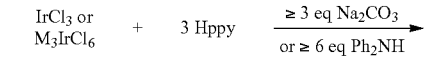

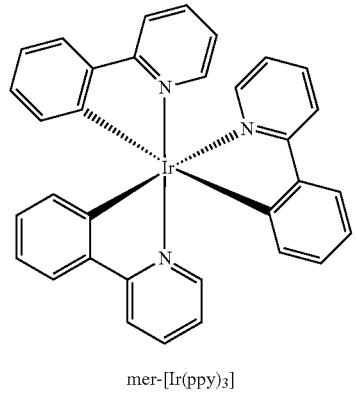

mer-[Ir(ppy)$_3$]

Example 7

Selective Synthesis of mer-[Ir(ppy)$_3$] by Using an Organic Base

IrCl$_3$ (24.1 mg, 0.068 mmole), 2-phenylpyridine (33.9 mg, 0.212 mmole) and Ph$_2$NH (86.2 mg, 0.415 mmole) were placed in a Teflon-lined autoclave, and then deionized water (10 ml) was added thereto. Subsequently, the autoclave was sealed and heated to perform reaction for 24 hours in an oven at 200° C. After cooling, filtration was performed via a filter funnel, and collected solids are washed with large amount of water, and then recrystallized from dichloromethane/hexane. Yellow powder of 0.039 g in a yield of 87% was obtained after drying.

Example 8

Selective Synthesis of fac-[Ir(ppy)$_3$] by Using an Organic Base

IrCl$_3$ (22.5 mg, 0.064 mmole), 2-phenylpyridine (31.6 mg, 0.200 mmole) and Ph$_2$NH (39.8 mg, 0.192 mmol) were placed in a Teflon-lined autoclave, and then deionized water (10 ml) was added thereto. Subsequently, the autoclave was sealed and heated to perform reaction for 48 hours in an oven at 200° C. After cooling, filtration was performed via a filter funnel, and collected solids were washed with large amount of water and then recrystallized from dichloromethane/hexane. Yellow powder of 0.0361 g in a yield of 86% was obtained after drying.

Example 9

Selective Synthesis of fac-[Ir(ppy)$_3$] by Using an Inorganic Base

IrCl$_3$ (22.5 mg, 0.064 mmole), 2-phenylpyridine (31.5 mg, 0.212 mmole) and Na$_2$CO$_3$ (10.4 mg, 0.098 mmole) were placed in a Teflon-lined autoclave, and then deionized water (10 ml) was added thereto. Subsequently, the autoclave was sealed and heated to perform reaction for 48 hours in an oven at 200° C. After cooling, filtration was performed via a filter funnel, and collected solids were washed with large amount of water and then recrystallized from dichloromethane/hexane. Yellow powder of 0.0373 g in a yield of 89% was obtained after drying.

Example 10

Selective Synthesis of mer-[Ir(ppy)$_3$] by Using an Inorganic Base

IrCl$_3$ (23.3 mg, 0.066 mmole), 2-phenylpyridine (33.6 mg, 0.212 mmole) and Na$_2$CO$_3$ (21.0 mg, 0.198 mmole) were placed in a Teflon-lined autoclave, and then deionized water (10 ml) was added thereto. Subsequently, the autoclave was sealed and heated to perform reaction for 24 hours in an oven at 150° C. After cooling, filtration was performed via a filter funnel, and collected solids were washed with large amount of water and recrystallized from dichloromethane/hexane. Yellow powder of 0.0375 g in a yield of 87% was obtained after drying.

The iridium complexes, fac-[Ir($C_{11}NR_8$)$_3$] or mer-[Ir($C_{11}NR_8$)$_3$], can be selectively prepared from a complex of IrCl$_3$ or M$_3$IrCl$_6$ (M is Li, Na or K) by controlling the amount of the added base relative to that of IrCl$_3$ or M$_3$IrCl$_6$ as follows.

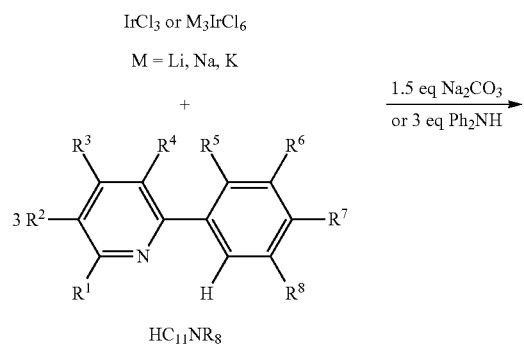

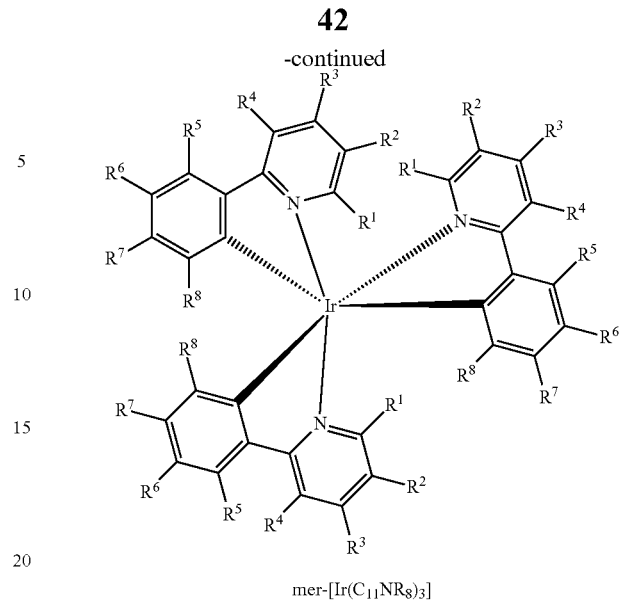

mer-[Ir(C₁₁NR₈)₃]

Herein, M is Na, Li or K; and each of $R^1$, $R^2$, $R^3$, $R^4$, $R^5$, $R^6$, $R^7 R^8$, independently, is hydrogen, deuterium, halogen, alkyl, alkenyl, alkynyl, alkoxy, alkenoxy, alkynoxy, cycloalkyl, cycloalkenyl or aryl; or $R^x$ and $R^{x+1}$ taken together is alkylene alkenylene, haloalkylene or haloalkenylene, x being an integer of 1 to 7.

Although the present invention has been explained in relation to its preferred embodiment, it is to be understood that many other possible modifications and variations can be made without departing from the spirit and scope of the invention as hereinafter claimed.

What is claimed is:

1. A method for preparing a compound represented by the following formula (VIII), (VIII)

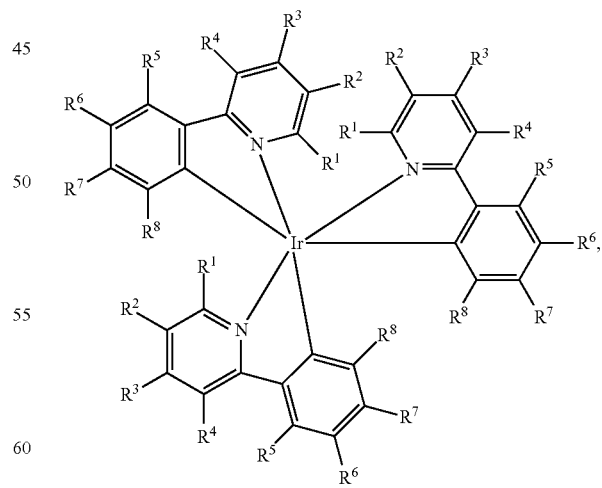

fac-[Ir(C₁₁NR₈)₃]

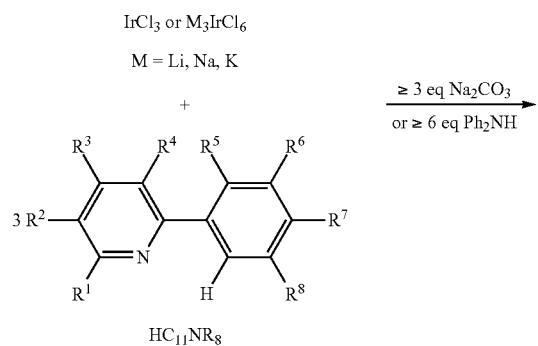

wherein the compound of the formula (VIII) is either a meridional isomer represented by the following formula (IX) or a facial isomer represented by the following formula (X),

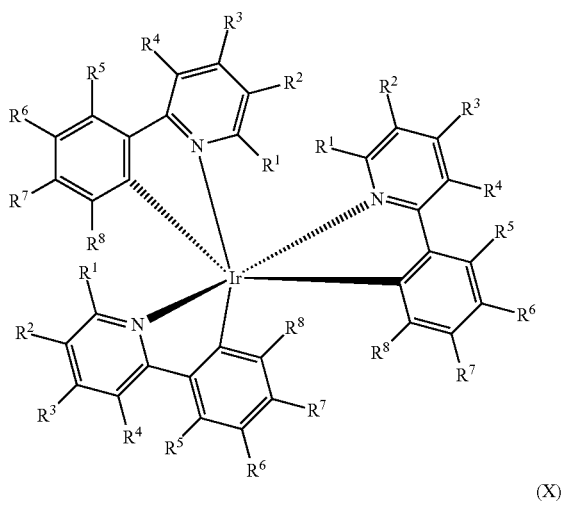

(IX)

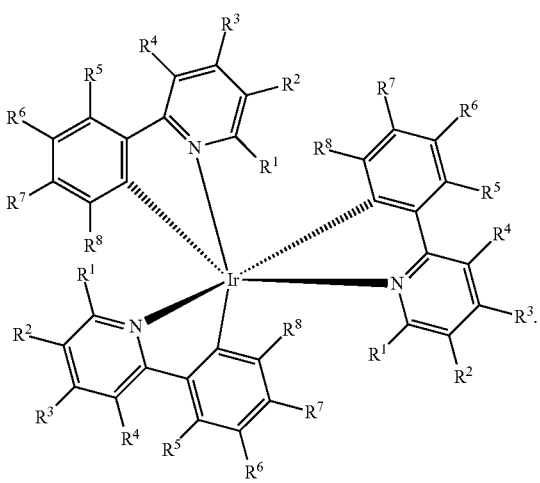

(X)

including a step of reacting IrCl$_3$ or M$_3$IrCl$_6$ with a base and a compound of the following formula (VI) in water,

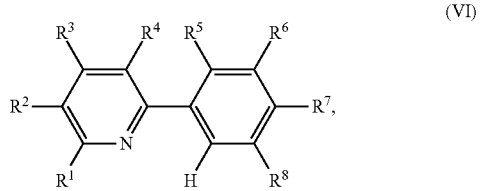

(VI)

wherein

M is Li, Na or K; and each of R$^1$, R$^2$, R$^3$, R$^4$, R$^5$, R$^6$, R$^7$ and R$^8$, independently, is hydrogen, deuterium, alkyl, alkenyl, alkynyl, halogen, alkoxy, alkenoxy, alkynoxy, haloalkyl, haloalkenyl, haloalkynyl, cycloalkyl, cycloalkenyl or aryl; or R$^x$ and R$^{x+1}$ taken together is alkylene, alkenylene, haloalkylene or haloalkenylene, x being an integer of 1 to 7.

2. The method as claimed in claim 1, wherein each of R$^1$, R$^2$, R$^3$, R$^4$, R$^5$, R$^6$, R$^7$ and R$^8$, independently, is hydrogen, deuterium, C$_{1-30}$ alkyl, C$_{2-30}$ alkenyl, C$_{2-30}$ alkynyl, halogen, C$_{1-30}$ alkoxy, C$_{2-30}$ alkenoxy, C$_{2-30}$ alkynoxy, C$_{1-30}$ haloalkyl, C$_{2-30}$ haloalkenyl, C$_{2-30}$ haloalkynyl, C$_{5-14}$ cycloalkyl, C$_{5-14}$ cycloalkenyl or C$_{6-14}$ aryl; or R$^x$ and R$^{x+1}$ taken together is C$_{3-12}$ alkylene, C$_{3-12}$ alkenylene, C$_{3-12}$ haloalkylene or C$_{3-12}$ haloalkenylene, x being an integer of 1 to 3 or 5 to 7; or R$^4$ and R$^5$ taken together is C$_{1-10}$ alkylene, C$_{2-10}$ alkenylene, C$_{1-10}$ haloalkylene or C$_{2-10}$ haloalkenylene.

3. The method as claimed in claim 1, wherein each of R$^1$, R$^2$, R$^3$, R$^4$, R$^5$, R$^6$, R$^7$ and R$^8$, independently, is hydrogen, deuterium, C$_{1-10}$ alkyl, C$_{2-10}$ alkenyl, C$_{2-10}$ alkynyl, halogen, C$_{1-10}$ alkoxy, C$_{2-10}$ alkenoxy, C$_{2-10}$ alkynoxy, C$_{1-10}$ haloalkyl, C$_{2-10}$ haloalkenyl, C$_{2-10}$ haloalkynyl, C$_{5-10}$ cycloalkyl, C$_{5-10}$ cycloalkenyl or C$_{6-10}$ aryl; or R$^x$ and R$^{x+1}$ taken together is C$_{3-8}$ alkylene, C$_{3-8}$ alkenylene, C$_{3-8}$ haloalkylene or C$_{3-8}$ haloalkenylene, x being an integer of 1 to 3 or 5 to 7; or R$^4$ and R$^5$ taken together is C$_{1-6}$ alkylene, C$_{2-6}$ alkenylene, C$_{1-6}$ haloalkylene or C$_{2-6}$ haloalkenylene.

4. The method as claimed as claim 1, wherein the base is an organic base or an inorganic base.

5. The method as claimed as claim 1, wherein the compound of the formula (VI) is

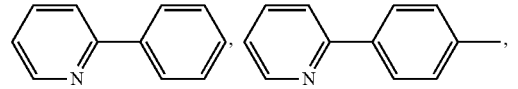

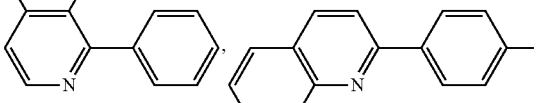

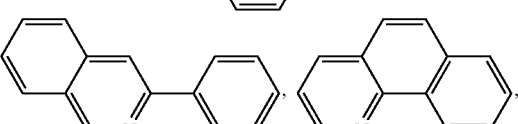

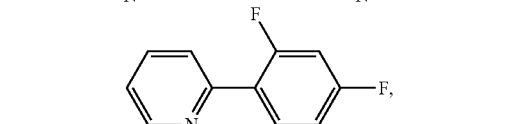

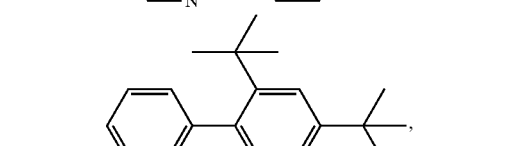

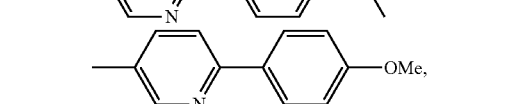

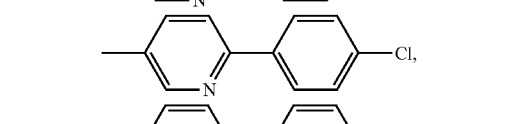

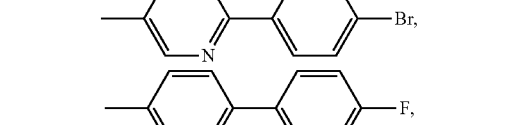

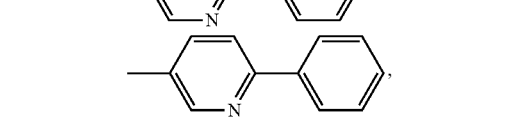

-continued

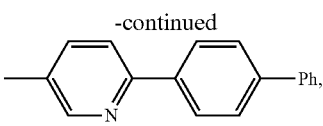

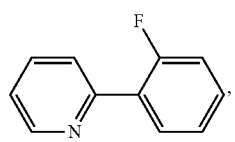

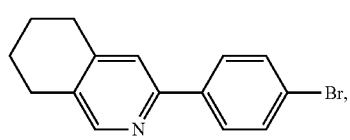

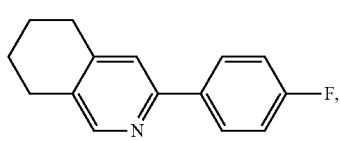

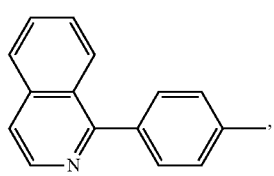

6. The method as claimed as claim 1, wherein the base is Na$_2$CO$_3$.

7. The method as claimed as claim 1, wherein the base is Ph$_2$NH.

8. The method as claimed as claim 6, wherein the compound of the formula (VIII) is a meridional isomer represented by the following formula (IX) when the amount of Na$_2$CO$_3$ is 1.5 equivalents relative to that of IrCl$_3$ or M$_3$IrCl$_6$ or a facial isomer represented by the following formula (X) when the amount of Na$_2$CO$_3$ is 3 equivalents relative to that of IrCl$_3$ or M$_3$IrCl$_6$, (IX)

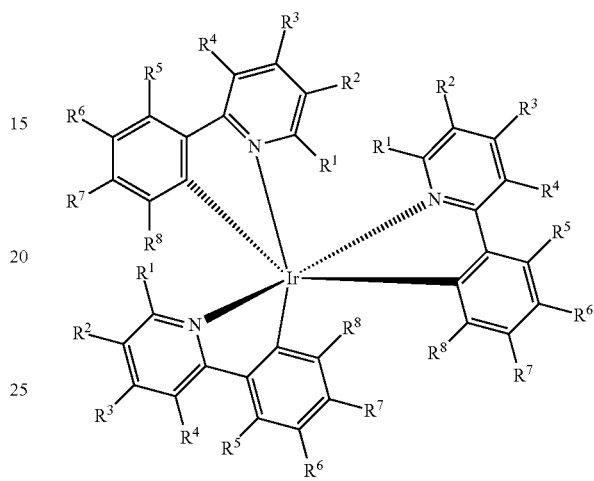

(X)

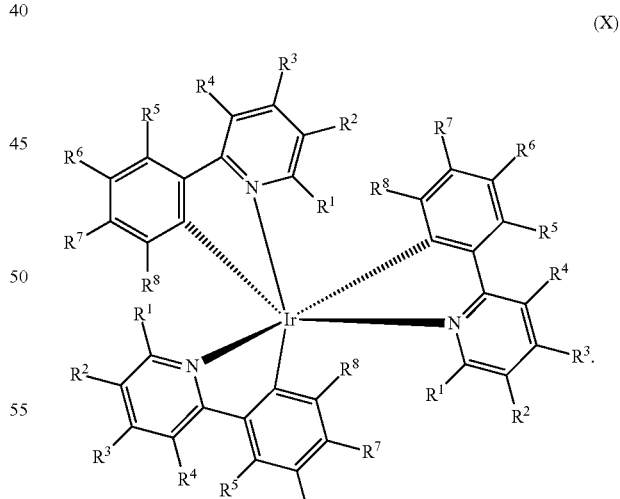

9. The method as claimed as claim 7, wherein the compound of the formula (VIII) is a meridional isomer represented by the following formula (IX) when the amount of Ph$_2$NH is 3 equivalents relative to that of IrCl$_3$ or M$_3$IrCl$_6$ or a facial isomer represented by the following formula (X) when the amount of Ph$_2$NH is 5 equivalents relative to that of IrCl$_3$ or M$_3$IrCl$_6$,

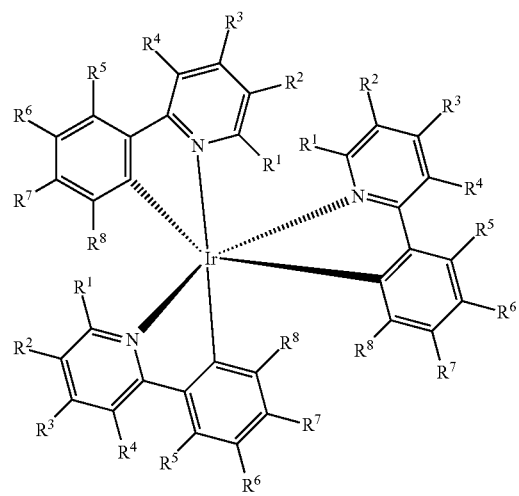
(IX)
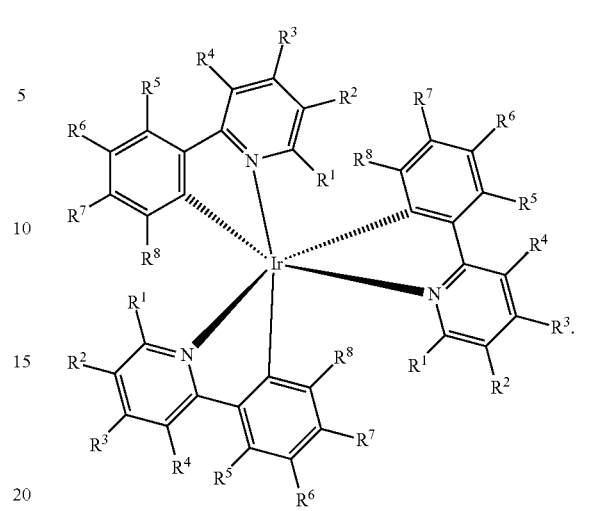
(X)
* * * * *